United States Patent
Harpham et al.

(10) Patent No.: US 10,814,047 B2
(45) Date of Patent: Oct. 27, 2020

(54) FLUID COLLECTION SYSTEMS AND METHODS OF USE

(71) Applicant: ALLEGIANCE CORPORATION, Waukegan, IL (US)

(72) Inventors: Raymond Reade Harpham, Columbus, OH (US); Brent Lee Burchfield, Powell, OH (US); Kok Hern Law, Singapore (SG); Rajesh Gladwin Dharmadas, Singapore (SG); Wei Chen Lie, Singapore (SG); Robert John Weinberg, Spring Grove, IL (US); Stephany Chang, Chicago, IL (US); Stacey Hoebel Burgardt, Chicago, IL (US); Matthew Michael Bruggeman, Columbus, OH (US); David James Stroud, Dublin, OH (US); Talya Mathein, Waukegan, IL (US)

(73) Assignee: ALLEGIANCE CORPORATION, Waukegan, IL (US)

( * ) Notice: Subject to any disclaimer, the term of this patent is extended or adjusted under 35 U.S.C. 154(b) by 672 days.

(21) Appl. No.: 15/497,201

(22) Filed: Apr. 25, 2017

(65) Prior Publication Data

US 2017/0304511 A1    Oct. 26, 2017

Related U.S. Application Data

(60) Provisional application No. 62/380,474, filed on Aug. 28, 2016, provisional application No. 62/380,472, (Continued)

(51) Int. Cl.
*A61M 1/00* (2006.01)

(52) U.S. Cl.
CPC ........ *A61M 1/0035* (2014.02); *A61M 1/0017* (2014.02); *A61M 1/0029* (2014.02); (Continued)

(58) Field of Classification Search
CPC .............. A61M 1/0035; A61M 1/0017; A61M 1/0029; A61M 1/0096; A61M 1/0052 (Continued)

(56) References Cited

U.S. PATENT DOCUMENTS

| 3,719,197 A | 3/1973 | Pannier et al. |
| 3,745,999 A | 7/1973 | Deaton |

(Continued)

FOREIGN PATENT DOCUMENTS

| EP | 0525493 A1 | 2/1993 |
| EP | 1225930 B1 | 11/2006 |

(Continued)

OTHER PUBLICATIONS

Coopdech, QinPot, retrieved on Dec. 15, 2014, 10 pages.

(Continued)

*Primary Examiner* — Andrew J Mensh
(74) *Attorney, Agent, or Firm* — Arent Fox LLP

(57) ABSTRACT

Fluid collection systems and methods are disclosed which may utilize suction to draw fluids into containers for storage and eventual disposal. The system may utilize rigid or semi-rigid canisters to provide a chamber in which fluids may be collected under negative pressure, stored, and transported. The system may utilize disposable or reusable flexible, semi-rigid, or rigid liners for isolating fluid and liquid waste from the walls of the canister. In various embodiments, either a single canister assembly or multiple canister assemblies are mounted to a manifold, the manifold being (Continued)

configured to support each canister assembly and/or provide a connection to a source of suction for each canister assembly.

16 Claims, 36 Drawing Sheets

Related U.S. Application Data filed on Aug. 28, 2016, provisional application No. 62/327,435, filed on Apr. 25, 2016.

(52) U.S. Cl.
CPC ......... *A61M 1/0096* (2014.02); *A61M 1/0052* (2014.02); *A61M 1/0056* (2013.01); *A61M 2205/581* (2013.01); *A61M 2205/582* (2013.01); *A61M 2205/583* (2013.01); *A61M 2209/08* (2013.01)

(58) Field of Classification Search
USPC ......................................................... 604/319
See application file for complete search history.

(56) References Cited

U.S. PATENT DOCUMENTS

| | | | |
|---|---|---|---|
| 4,465,485 A | | 8/1984 | Kashmer et al. |
| 4,681,571 A | | 7/1987 | Nehring |
| 5,203,470 A | | 4/1993 | Brown |
| 5,470,324 A | | 11/1995 | Cook et al. |
| 5,725,516 A | | 3/1998 | Cook et al. |
| 6,056,730 A | * | 5/2000 | Greter ................ A61M 1/0001 600/578 |
| 6,056,731 A | * | 5/2000 | Koetke ............... A61M 1/0001 604/317 |
| 6,093,230 A | | 7/2000 | Johnson, III et al. |
| 6,270,488 B1 | | 8/2001 | Johnson et al. |
| 6,409,220 B1 | | 6/2002 | Wing et al. |
| 6,499,495 B2 | | 12/2002 | Jeng |
| 6,780,309 B2 | | 8/2004 | Haldopoulos et al. |
| 7,481,243 B2 | | 1/2009 | Michaels et al. |
| 7,635,359 B2 | | 12/2009 | Nakazawa et al. |
| 8,025,173 B2 | | 9/2011 | Michaels |
| 8,100,874 B1 | | 1/2012 | Jordan et al. |
| 8,118,796 B2 | | 2/2012 | Rajamaki |
| 8,172,817 B2 | | 5/2012 | Michaels et al. |
| 8,460,256 B2 | | 6/2013 | Michaels et al. |
| 8,500,706 B2 | | 8/2013 | Michaels et al. |
| 2006/0079853 A1 | | 4/2006 | Christensen et al. |
| 2009/0005747 A1 | | 1/2009 | Michaels et al. |
| 2009/0287190 A1 | | 11/2009 | Shippert |
| 2010/0270222 A1 | | 10/2010 | Lauer |
| 2011/0178482 A1 | | 7/2011 | Michaels et al. |
| 2011/0180566 A1 | | 7/2011 | Kobashi et al. |
| 2015/0291352 A1 | | 10/2015 | Morgan et al. |

FOREIGN PATENT DOCUMENTS

| | | |
|---|---|---|
| WO | 0124846 A1 | 4/2001 |
| WO | 2015055893 A1 | 4/2015 |

OTHER PUBLICATIONS

Coopdech, QinPot, Retrieved on Dec. 15, 2014, Retrieved from the Internet URL: http://www.brandcom.ro/data_editor/QIN%20POT%20romana%20andreea(1).pdf, 21 pages.
Daiken Medical Co. Ltd., Coopdech, QinPot, Infection Control, Retrieved on Dec. 15, 2014, Retrieved from the Internet URL: http://www.daiken-iki.co.jp/en/pi/in_qp.html. 2 pages.
Daiken Medical Co. Ltd., Coopdech, QinPot, The Wall Mount Type Closed 1000mL Suction System, Apr. 2011. 2 pages.
International Preliminary Report on Patentability and Written Opinion for PCT/US2016/057413 dated Apr. 17, 2018, 7 pages.
International Search Report and Written Opinion for Application No. PCT/US2016/057413, dated Jan. 30, 2017, 12 pages.
International Search Report and Written Opinion for Application No. PCT/US2017/029494, dated Sep. 7, 2017, 14 pages.

* cited by examiner

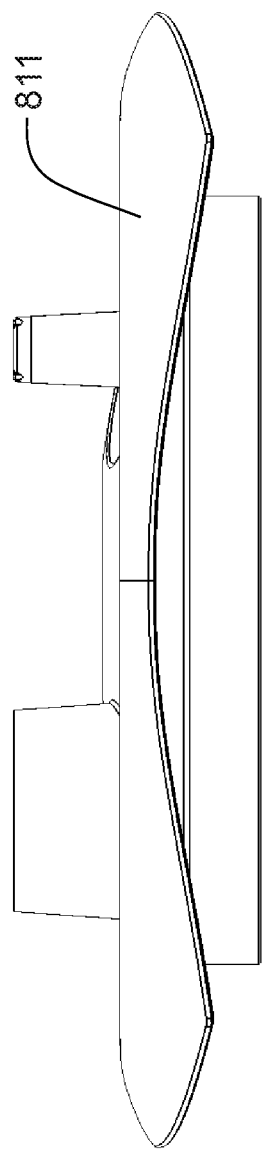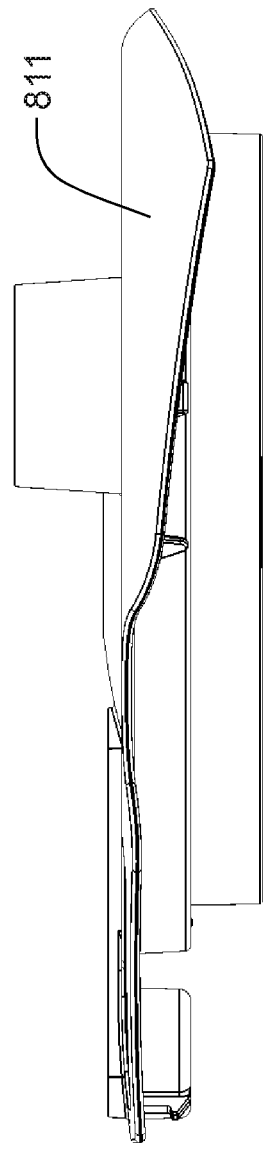

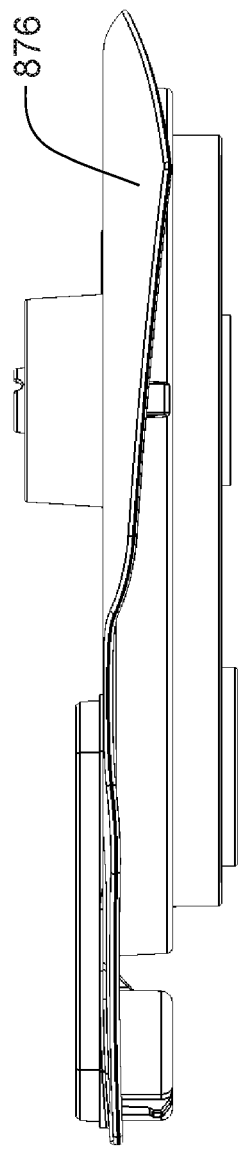
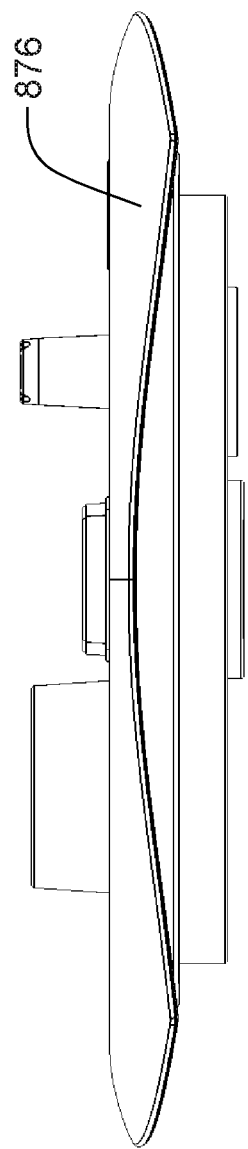

FLUID COLLECTION SYSTEMS AND METHODS OF USE

CLAIM OF PRIORITY

This application claims priority to, and the benefit of, U.S. Provisional Application Ser. No. 62/327,435, entitled "FLUID COLLECTION SUCTION CANISTER SYSTEM WITH TUBELESS TANDEM CONNECTOR AND RELATED METHODS" and filed on Apr. 25, 2016, the entire contents of which is incorporated herein by reference; and this application claims priority to, and the benefit of, U.S. Provisional Application Ser. No. 62/380,472, entitled "FLUID COLLECTION SYSTEMS AND METHODS OF USE" and filed on Aug. 28, 2016, the entire contents of which is incorporated herein by reference; and this application claims priority to, and the benefit of, U.S. Provisional Application Ser. No. 62/380,474, entitled "FLUID COLLECTION SYSTEMS AND METHODS OF USE" and filed on Aug. 28, 2016, the entire contents of which is incorporated herein by reference.

BACKGROUND

Field of the Invention

Fluid collection systems and methods as disclosed herein may be related to the field of medical fluid collection, disposal and other related methods, and more specifically, certain aspects may relate to medical waste fluid collection and/or disposal systems that utilize a canister for directly or indirectly storing various fluids and liquid waste; such canisters may include a flexible, semi-rigid or rigid liner for isolating fluid from the canister walls.

Background of the Technology

The medical environment, which could include operating rooms, emergency rooms and other healthcare facilities, generates liquid waste. Liquid waste may include secretions removed from a patient's body, which may include blood and other bodily fluids, irrigation liquids, or other fluids, such as suspended solids and various other particles. A typical waste canister of the related art is a storage container in which negative pressure (also interchangeably referred to herein as "suction" or "vacuum") is communicated so as to thereby create negative pressure inside the canister to draw in or drain fluids and liquid waste from at or near a drainage or surgical site. Vapors, smoke, particles, and small solids are also commonly drawn into the suction canister. Gasses containing solids are typically filtered and evacuated from the canister, while fluids and liquid waste are collected in the canister. Canister systems may include a flexible, semi-rigid or rigid liner to isolate fluids and liquid waste from the canister walls. Flexible liners are frequently secured to the lid in an expanded state or in a compacted or collapsed state and may expand to fit inside the canister walls. Fluids and liquid waste may enter through a port in the lid or canister and fill the canister or liner. After use, the flexible or semi-flexible liner may be sealed, removed from the canister and disposed of in a desired manner. In a system that isolates fluid and liquid waste from the outer walls of the canister, the canister may be reused with multiple new lid and/or liner assemblies. The canisters may be removed and discarded or periodically sanitized and reused.

Used individually, a canister assembly typically requires at least two ports for ordinary use: (1) a vacuum or suction port for applying suction to the interior of the canister; and (2) a patient port to allow fluid to enter the interior of the canister. However, when fluid volumes exceed the capacity of a single canister, multiple canisters are commonly connected in a serial configuration (i.e., in tandem) such that when a first canister is filled to capacity, excess fluid collected in the first canister may be drawn into the second canister via a tandem connection, typically a tandem tube connection between a tandem port (also known as an ortho port) of the first lid and the patient port of the second lid. Commonly, as many as six or more canisters are connected in serial to accommodate large volumes of fluid generated during certain medical procedures (e.g., surgery). At present, flexible tubes coupled to end fittings are typically employed to connect the various ports to either the vacuum source, the patient or fluid collection instrument, and other serial-connected canisters. Typically, in the related art, the above-mentioned fluid collection systems and methods include a vacuum system for creating a negative pressure inside a single or multiple canisters. Tubing may connect a series of canisters for increasing fluid and liquid waste capacity. When a series of canisters is used, a significant number of tubes may be necessary for connecting each canister. The use of, attachment, and removal of numerous tubes may be visually unappealing, distracting, and hazardous. Because the process of connecting multiple canisters can be complicated and time-consuming, the need arises for an improved system of setting up and connecting a single or series of canisters.

SUMMARY

Among others, various aspects of the present disclosure may include a fluid collection system that utilizes suction to draw fluids into containers for storage and eventual disposal. The system may utilize rigid or semi-rigid canisters to provide a chamber in which fluids may be collected under negative pressure, stored, and transported. In certain aspects of the present disclosure, the system may utilize disposable or reusable flexible, semi-rigid, or rigid liners for isolating fluid and liquid waste from the walls of the canister. Such canisters and liners may either be disposable or reusable.

In one aspect, the system includes one or more canister assemblies including at least a canister body and a lid. The lid may cover an opening in the canister body and form a seal with the canister body. The canister body and lid may be configured to be attached using an interference fit, mating threads provided at the canister body and the lid, deformable tabs for creating a locking connection between the canister and lid, and/or any other method and features suitable for allowing a positive connection between the lid and canister. The canister body or lid may include visible, audible, or other indicia to indicate a positive connection between the canister body and lid. In some embodiments, a positive connection is not required because the canister body and lid may be configured to form a seal as a result of suction applied to the interior of the canister.

Each lid and/or canister may include one or more vacuum ports or connections for attachment of a vacuum source, and one or more patient or instrument ports or connections for connecting to a fluid source such as a patient fluid suction instrument or drainage tube. Each lid may further include a tandem port for connecting to either the patient port or a separate tandem receiver port of an adjacent canister assembly. Each tandem connector and patient/tandem receiver port may be configured to interface such that multiple canisters may be used in a tandem configuration with the tandem connector of a first canister connecting with a patient/tandem receiver port of an adjacent container to increase the capacity of fluid storage. It will be appreciated by those skilled in the art that many of the features disclosed herein may also be implemented in connection with canister systems that lack a liner such that fluid is collected directly in the canister itself.

The ports may connect directly to a manifold or another canister assembly, or indirectly through the canister body or through the use of flexible, rigid, or semi-rigid tubing, for example. The lid may also include an opening or holder for receiving or housing a solidifier, which may be mounted to the lid as a separate component, or molded into or attached to the lid. The lid may further include a handle that may be integrally formed with the lid, or fixed to or pivotally attached to the lid.

In one example configuration, each canister assembly includes a rigid or semi-rigid lid that has a flexible or semi-flexible liner permanently or removably attached to the lid. The lid and liner assembly is configured to fit into and to be separately removable from a rigid or semi-rigid canister. In these configurations, negative pressure applied at the interior of the liner could cause the liner to collapse or partially collapse. Therefore, it may be advantageous to apply suction to the space between the exterior of the liner and the interior surface of the canister wall (generally referred to herein as the "interstitial space"), in a manner such that negative pressure is created in the interstitial space. The negative pressure in the interstitial space acts to pull the liner outward towards the inner canister walls, and prevents the liner from collapsing when negative pressure is present at the interior of the liner.

One non-limiting aspect includes either a single canister assembly or multiple canister assemblies mounted to a manifold, the manifold being configured to support the canister assembly and/or provide a connection to a source of suction for each canister assembly. In one configuration, the manifold provides a common suction chamber that is in communication with a main source of suction, such as a central vacuum system of a medical facility or an independent vacuum generator that is integral with or connected to the manifold. The manifold may include a plurality of suction channels branching off from the common suction chamber. Each suction channel provides an auxiliary vacuum source for supplying suction to one or more canister assemblies. Further, the manifold may include one or more valves for controlling the amount of suction supplied to, or an on/off state of, the main suction chamber and/or one or more of the auxiliary vacuum source connections individually. In another aspect, the manifold body may include valves operable by levers, switches, or buttons for selectively opening and/or closing communication of the vacuum path with each auxiliary vacuum source connection. The switches or buttons may include visual indicia or otherwise indicate to the user that the valve controlling the vacuum path is open or closed. The auxiliary sources may also be configured to shut-off automatically when the corresponding canister is full.

In some variations, suction supplied by the main vacuum source may be distributed to each canister assembly through the manifold via an auxiliary vacuum source connection. The auxiliary vacuum source connection may communicate with the interstitial space and the interior of the liner via the lid, the canister body, or both. The auxiliary vacuum source connection may provide suction individually to the interstitial space or to the interior of the liner. Alternatively, the auxiliary vacuum source connection may provide suction to both the interior of the liner and the interstitial space. Further in an example variation in which only a single container is used, the main vacuum source may be directly connected to the interior of the liner and/or the interstitial space via one or both of the lid or canister body. It will be appreciated by those skilled in the art that many of the features disclosed herein may be implemented in connection with canister systems that lack a liner, such that fluid is collected directly within the canister itself.

The canisters, lids/liners and manifold may be arranged in various configurations and the system may have multiple mounting options for supporting either a single canister assembly or a plurality of canister assemblies in a desired orientation with respect to the manifold. In some variations, the mounting configuration may hold one or more canisters and/or lids in a fixed position and orientation relative to other mounted canisters and/or lids. The mounting of the canister assembly or plurality of canister assemblies may include a mobile holder, such as a rolling stand or cart, or a stationary holder, such as a wall bracket or surface mount. In one aspect, a mounting portion of the holder for each canister assembly may be shaped to substantially match a corresponding mounting portion of the canister and/or lid, such that the holder interfaces and stably holds the canister body and/or lid when a user delivers the canister and/or lid into the holder. In another configuration, the holder and/or manifold may interface with an extension protruding from the canister lid. Other aspects may include the holder and/or manifold interfacing with an extension protruding from the canister body. The mounting portions may fit into corresponding mounting portions on the manifold body or holder to support the canister assembly. Each of the abovementioned mounting options may include a storage section for mounting various accessories, including suction tubing, tubing connectors, suction instruments such as a yankauer, solidifying and/or disinfecting agents, and other related accessories. Non-limiting examples of a storage section may include a hook-shaped bracket, a drawer, or a shelf.

Various configurations may correspond with the above-mentioned mounting options. For example, the canister body may have a protruding mounting portion that may include an internal vacuum passage. The internal vacuum passage may communicate with either the common suction chamber or an auxiliary vacuum source passageway. In various embodiments, the auxiliary vacuum source passageway may branch into separate passageways leading to separate auxiliary vacuum source connections, each for communicating suction to a single canister assembly. In these configurations, a first opening may communicate suction to the interstitial space either directly via an internal passage located within the canister body or via a passage in the lid that is in communication with an interstitial opening in the lid located between the exterior of the liner and the interior of the canister wall. A second opening in the manifold may communicate with an internal passage in the lid to supply suction to the interior of the liner. In some embodiments, the second opening in the manifold may communicate with a second internal passage in the canister body, which communicates with an internal passage in the lid to supply suction to the interior of the liner.

In various other configurations, suction may be provided to the canister assembly at a single connection at the lid and may be routed through the lid and to an interstitial suction opening located between the liner and canister body, and the suction applied at the lid may be further routed so as to also communicate with the interior of the liner. Alternatively, suction may be provided at a single connection at the canister body and may be routed through a passage in the canister body to the interstitial space. The suction applied at the canister body may be further routed through a branch of the internal passage in the canister body so as to also communicate with a passageway in the lid that is in communication with the interior of the liner. Alternatively, suction applied at the interstitial space may be communicated to the interior of the liner via a passage in the lid having an opening in the lid located between the exterior of the liner and the inner canister wall.

In certain aspects, the lid includes a substantially rigid projection member extending distally outward from a central portion of the lid. A vacuum port is provided at a distal portion of the projection member and is configured to connect to a mating vacuum port provided at the mounting interface upon connecting the lid to a canister previously mounted to the mounting interface, or upon mounting the previously assembled canister, lid, and liner assembly to the mounting interface. In certain aspects, the projection member, or another keyed feature is configured to permit the canister assembly to be mounted to the bracket or stand only at one or more predetermined orientations. These predetermined orientations can be implemented to ensure consistent positioning and orientation of the patient, vacuum, and tandem ports of the lid relative to the mounting interface and to other mounted canister assemblies.

In certain aspects, the fluid collection system includes a support stand configured to support multiple canister assemblies. The bracket or support stand may be configured to hold the canister assemblies in a predetermined position and orientation relative to other canister assemblies mounted thereon. This feature can be implemented to ensure consistency in the position and orientation of the patient and tandem ports of each canister assembly relative to each other. More specifically, these features can be implemented to ensure that the tandem or patient port of a first mounted canister assembly is at a predetermined position and orientation relative to the tandem port of a second canister assembly mounted adjacent to the first canister assembly, and that the patient port of the second canister assembly is at a predetermined position and orientation relative to the tandem port of a third canister assembly mounted adjacent to the second canister assembly. This configuration provides consistent positioning of tubing connections and thereby simplifies setup and use of a serial connected fluid collection canister system and further reduces the likelihood of human error.

Although the predetermined positioning and orientation of the multiple serial connected canister system as described above can be implemented with traditional flexible tubing tandem connectors, the predetermined distance and orientation of the canister ports relative to one another advantageously enables the use of more rigid tandem connectors. In certain aspects, the fluid collection system includes a rigid or at least semi-rigid tandem connector arm coupled to a first lid of a first canister assembly. In certain aspects, the arm includes a port at a proximal end, a port at a distal end, and a channel or passageway that communicates the proximal and distal ports with each other. The proximal end of the arm is rotatably coupled with the first lid and the proximal port cooperates with a mating port in the first lid to communicate the interior of the first canister assembly liner with the distal port of the arm. The arm may be configured to rotate about its proximal end such that the distal port engages a mating tandem port or patient port of an adjacent canister assembly to communicate the interior of the adjacent canister assembly with the interior of the first canister assembly, thereby completing a tandem connection between the two canister assemblies. The arm or the lid, or both the arm and the lid, may include a valve configured to be open when the arm is extended (i.e., rotated away from a center of the lid) and closed with the arm is retracted to prevent leakage of fluid collected in the canister assembly.

While various aspects disclosed will be described in connection with a particular medical waste collection and disposal apparatus and/or method, one having ordinary skill in the art will appreciate that aspects of the present disclosure may be used in other suitable medical and non-medical applications, examples of which may include medical and/or non-medical cleaning devices and processes.

BRIEF DESCRIPTION OF THE FIGURES

Embodiments of the present disclosure are described by way of following drawings pointing out various details of the systems, devices and methods of the present disclosure. Example features and advantages of various aspects of the present disclosure will be better understood with the following descriptions, claims, and drawings, where:

FIG. 21 is a front view of a lid in accordance with aspects of the present disclosure.

FIG. 22 is a side view of a lid in accordance with aspects of the present disclosure.

FIG. 34 is a side view of a lid in accordance with aspects of the present disclosure.

FIG. 35 is a front view of a lid in accordance with aspects of the present disclosure.

Figure 1A:
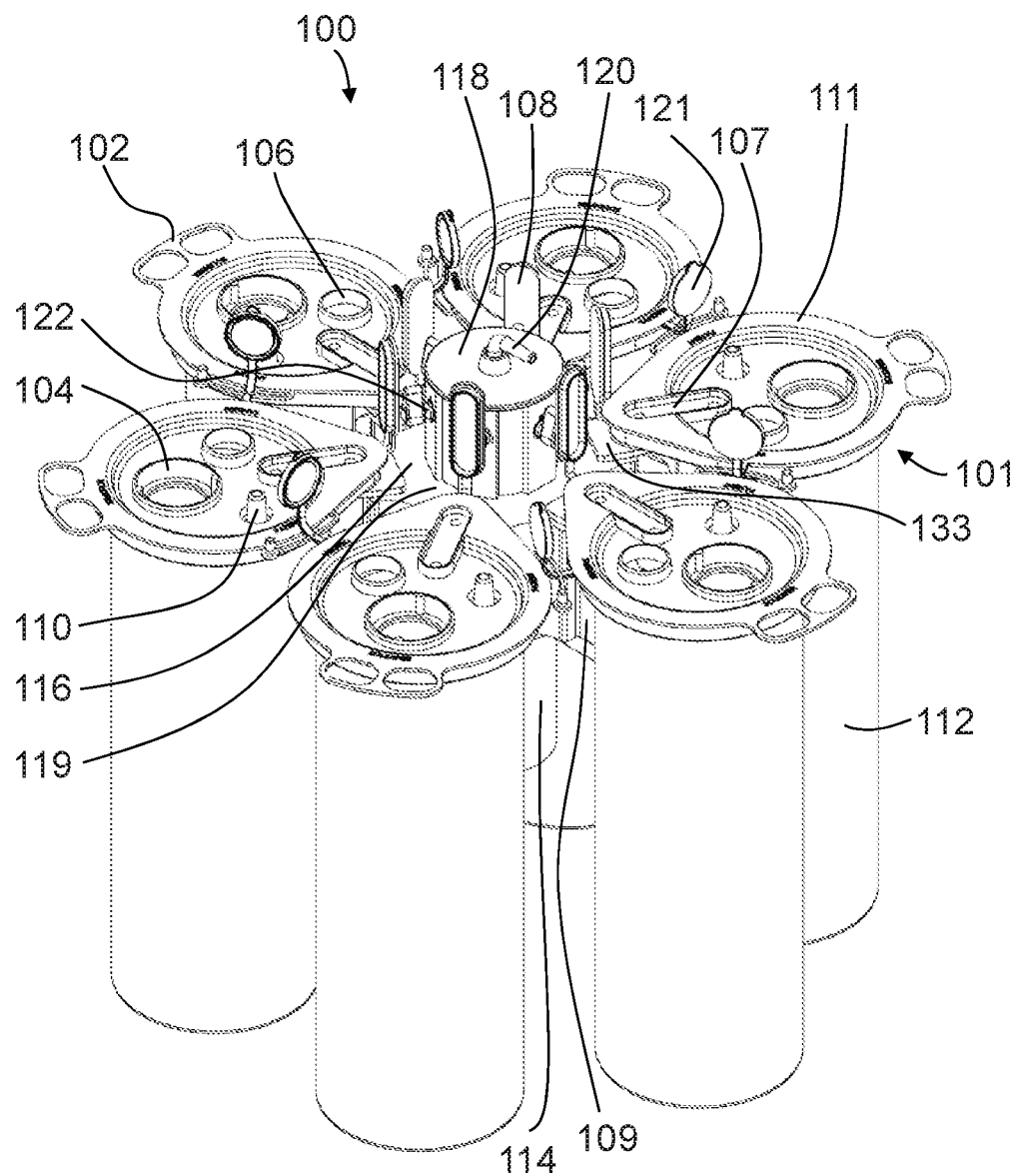
FIG. 1(a) is a perspective view of an example fluid collection system including multiple suction canister assemblies radially mounted to corresponding mounting interfaces of a manifold body, in accordance with aspects of the present disclosure.

It should be understood that the figures are diagrammatic and schematic representations of exemplary embodiments of the systems and methods of the present disclosure, and are neither limiting nor necessarily drawn to scale.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

Various aspects of the systems and devices disclosed herein may be illustrated by describing components that are connected, coupled, attached, bonded and/or joined together. As used herein, the terms "connected", "coupled", "attached", "bonded" and/or "joined" are used interchangeably to indicate either a direct connection between two components or, where appropriate, an indirect connection to one another through intervening or intermediate components. Additionally, unless otherwise specified, these terms are used interchangeably to indicate a connection in which one or more degrees of freedom are not rigidly constrained between two components (e.g., a pivoting connection, a translating connection, a pivoting and translating connection, an elastic connection, a flexible connection, etc.), or a rigid or substantially rigid connection in which all degrees of freedom are constrained or substantially constrained between the two components.

Relative terms such as "lower" or "bottom", "upper" or "top", and "vertical" or "horizontal" may be used herein to describe one element's relationship to another element illustrated in the drawings. It will be understood that relative terms are intended to encompass different orientations of the systems and devices in addition to the orientation depicted in the drawings. By way of example, if aspects of a fluid collection system as shown in the drawings are turned over, elements described as being on the "bottom" side of the other element would then be oriented on the "top" side of the other elements as shown in the relevant drawing. The term "bottom" can therefore encompass both an orientation of "bottom" and "top" depending on the particular orientation of the drawing.

The term "fluid" as used herein is not limited merely to referring to a state of matter as defined in the thermodynamic and/or fluid mechanics sense. The term "fluid" may also include any solid particles or gases that may incidentally flow with or without a liquid medium (e.g., irrigation fluid or blood, or other liquid) or that may be intentionally collected using a liquid medium. For example, if the fluid collection system is used in a surgical procedure, the term "fluid" may refer to a combination of liquid medium (e.g., irrigation fluid, blood, and other bodily liquid from the patient) and any solid particles including, but not limited to, resected tissue removed from the patient's body or harmful particles mixed with smoke or other particulates and/or gases, such as may be generated in connection with use of laser, cauterization, and/or other medical procedures. The term "fluid," as used herein may also refer to a liquid medium, solid particles, smoke, gases, particulates, and combinations thereof.

The term "interstitial space" as used herein is intended to encompass spaces that are in fluid communication with the space between the interior of the canister and the exterior surface of the liner but which are not necessarily located directly between the interior of the canister and the exterior of the liner. For example, in certain embodiments, the lid may include a skirt extending downward into the interior of the canister and which is offset inwardly from the canister wall. The liner may be secured to a lower end of the skirt such that a space is defined between the interior of the canister and the exterior of the skirt. The interstitial space is intended to include such space, even though it is arguably not located directly between the interior of the canister and the exterior of the liner.

Figure 1B:
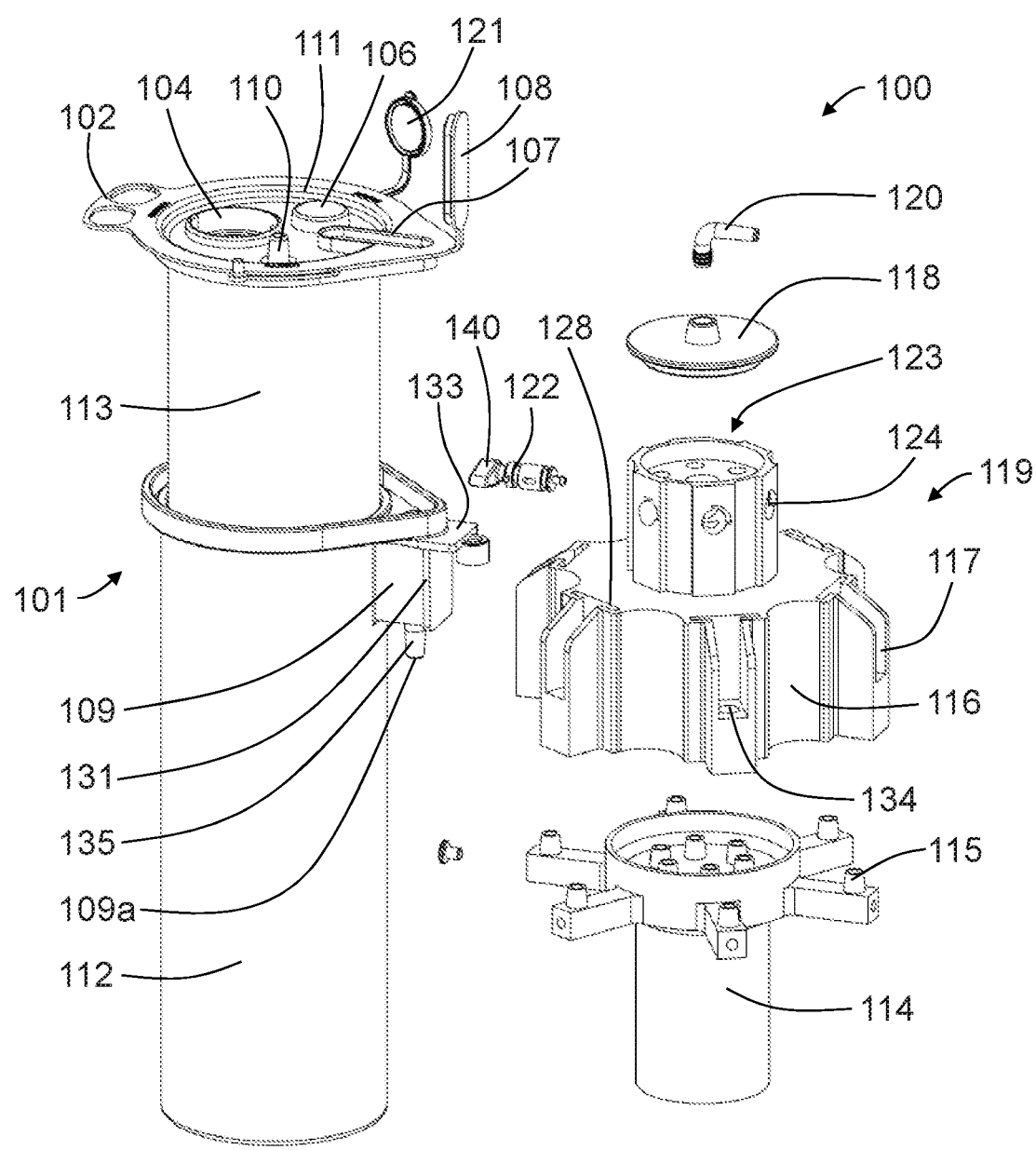
FIG. 1(b) is an exploded view of a canister assembly and a manifold assembly in accordance with aspects of the present disclosure.
Figure 2:
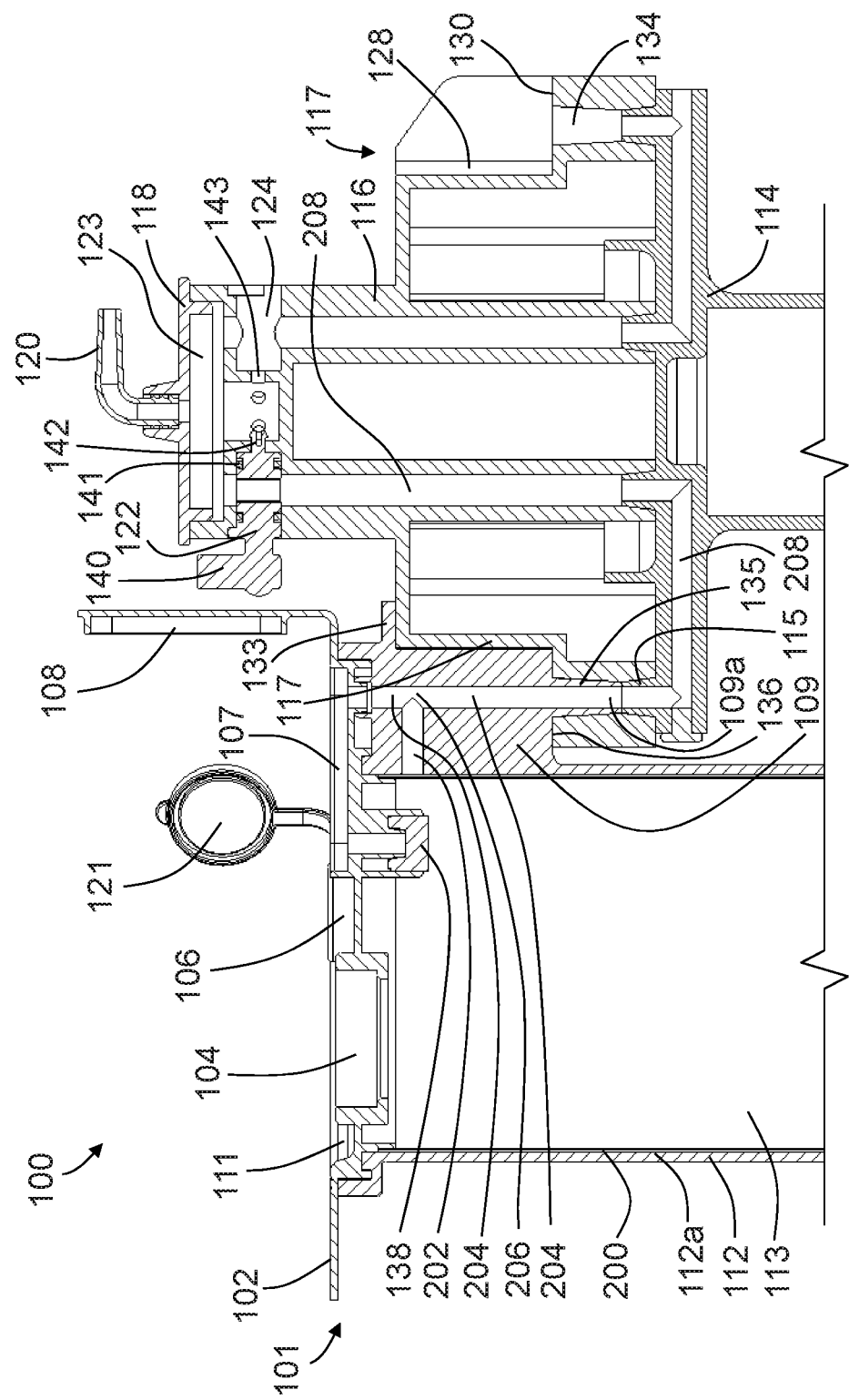
FIG. 2 is a sectional view of the example fluid collection system of FIG. 1, including a canister assembly mounted to the manifold, according aspects of the present disclosure.
Figure 3:
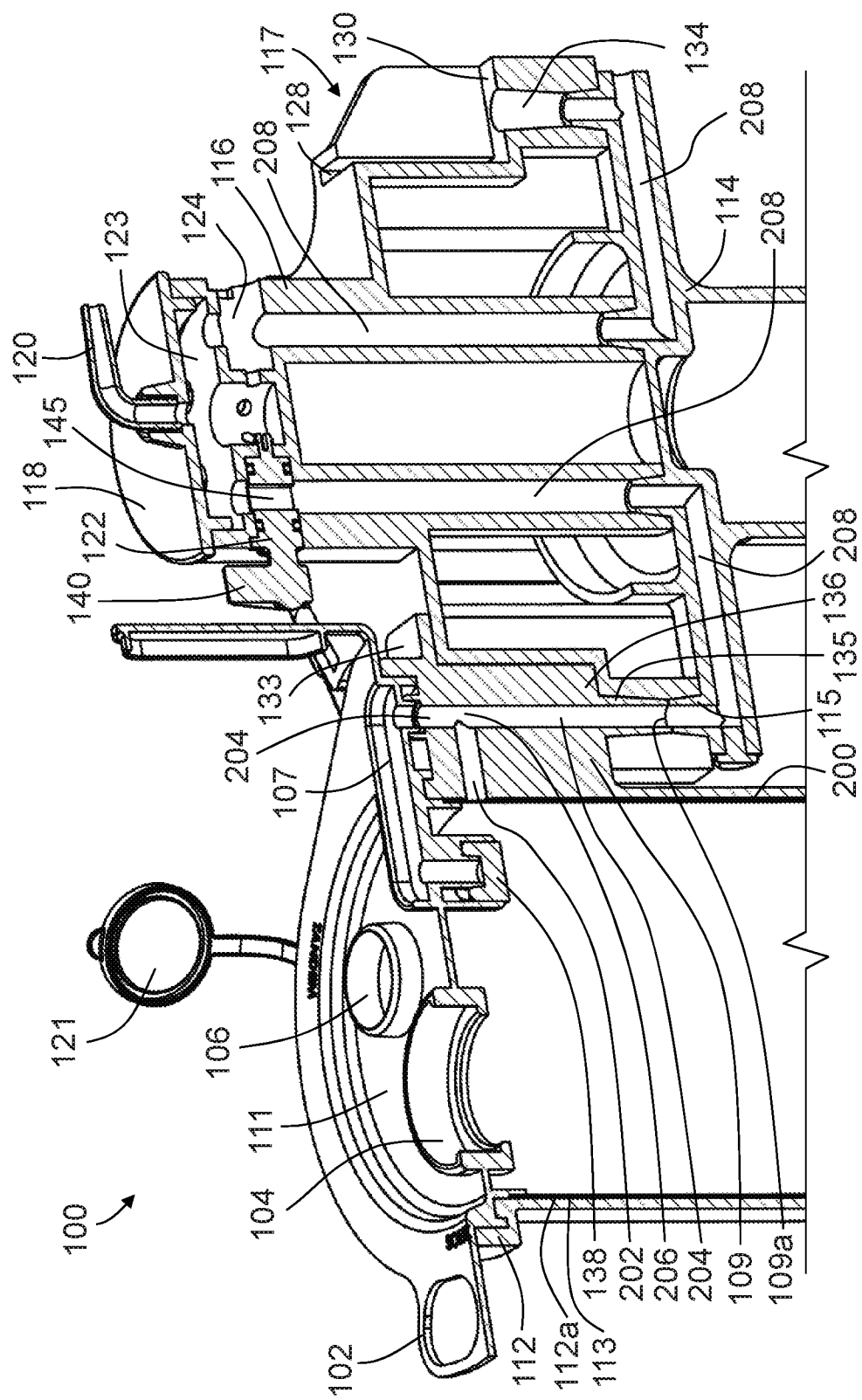
FIG. 3 is a perspective sectional view of the example fluid collection system of FIGS. 1 and 2, illustrating the vacuum path, manifold assembly, and interface between the canister and manifold body, according to aspects of the present disclosure.

One example fluid collection system in accordance with aspects of the present disclosure is illustrated in FIGS. 1-3. The non-limiting aspects illustrated in FIGS. 1(*a*) and 1(*b*) include a fluid collection system 100 having a plurality of canister assemblies 101, each having a canister body 112, including an opening 125, and a lid 111 configured to substantially seal the canister opening 125. Each canister assembly 101 is mounted to a manifold body 116 and/or manifold base 114. Each lid 111 may include an accessory opening 104 and a tandem port 106. The accessory opening 104 may be used for, as non-limiting examples, taking samples from or draining collected fluid, or introducing a solidifying or disinfecting agent into the collected waste fluid. The tandem port 106 may typically be used for connecting multiple canister assemblies in series, but may also be used for draining either the container body or a liner attached to the lid. The lid 111 includes at least one collection port 110 (referred to herein as a patient port 110). In the example illustrated in FIGS. 1(*a*) and 1(*b*), the lid 111 includes a lid vacuum passageway 107 for communicating suction from a vacuum source to the interior of the liner. Each lid may further include a handle or holder 102 and one or more port caps 121 that may be integrally molded with the lid 111 or tethered to the lid 111, or may be provided as separate pieces.

As illustrated in FIG. 1(*b*), the canister assembly 101 may further include a liner 113 for receiving collected fluids and isolating such fluids from the inner surface of the canister 112. The canister 112 may also include a mounting portion 109 for mounting the canister to a canister receiving portion 117 of the manifold 119. The mounting portion 109 may optionally include a vacuum opening 109*a* for communicating vacuum with the manifold auxiliary vacuum source connector 115 when the mounting portion 109 of the container is engaged with the canister receiving portion 117.

As illustrated in FIGS. 1(*a*) and 1(*b*), the manifold 119 may further include a vacuum source lid 118 and a vacuum source connecter 120 for communicating the manifold with a main vacuum source for the system 100. The lid 118 may enclose a common vacuum chamber 123 as illustrated in FIGS. 2 and 3. The manifold 119 may further include one or more vacuum control valves 122 for individually controlling communication of suction between the common vacuum chamber 123 and each canister assembly 101 via an auxiliary vacuum source path (see example auxiliary vacuum source passageway 208 illustrated in FIG. 2).

As illustrated in FIGS. 1 to 3, the manifold 119 may include a manifold base 114 and a manifold body 116. The manifold body 116 may further include an auxiliary vacuum source passageway 208 that communicates with the auxiliary vacuum source connector 115 in the manifold base 114. The manifold body 116 may include a single or multiple canister receiving portions 117 for receiving a canister mounting portion 109. Each mounting portion 109 may include a guide flange 131 or similar attaching feature, which may be received within a guide slot 128 (see FIG. 3) of the manifold body 116. The mounting portion 109 may further include a stop 133 for limiting motion of the canister 112 via contact with a transverse surface of the manifold body 116 when the canister 112 is mounted to the manifold body 116. Each canister receiving portion 117 may further include a base 130, which may contact a canister mounting base portion 136 (see FIG. 3) of each canister 112 when the canister is mounted to the manifold body 116. It will be appreciated by those skilled in the art that the mating portions of the canister and the manifold body may engage securely by utilizing interference fits, tapered elements, releasable locking features, such as elastic tabs or catches and corresponding slots, and various other mechanisms for releasably securing elements to each other. Further, the mounting portion 109 may include a connector portion 135 (see FIG. 3) to be received by a connector receiving portion 134 of the canister receiving portion 117 of the manifold body 116. For example, the connector portion 135 and connector receiving portion 134 may have complementary tapered surface geometry for mating engagement. The abovementioned mating surfaces between the mounting portion 109 and canister receiving portion 117 may optionally further include a single or plurality of seals for substantially sealing the interface between the auxiliary vacuum source connector 115 and the vacuum opening 109*a* of the canister mounting portion 109.

Each lid 111 may have a flexible or semi-flexible liner 113 permanently or removably attached to the lid 111. The liner 113 may be configured to fit into and to be separately removable from the canister 112. In the example configuration as illustrated in FIGS. 1 to 3, the mounting portion 109 of each canister 112 includes a primary vacuum passageway 204 in communication with the corresponding auxiliary vacuum source connector 115. An interstitial vacuum passageway 202 branches off of the primary vacuum passageway 204 at a junction 206 provided in the mounting portion 109 of the canister 112. The interstitial vacuum passageway 202 communicates suction to the interstitial space 200. Suction is applied to the interior of the liner 113 via a lid vacuum passageway 107 in communication with the primary vacuum passageway 204 in the canister mounting portion 109 (see FIG. 2). The lid passageway 107 may include as a wall portion a lid vacuum passageway cap 108. The lid vacuum passageway cap 108 may be either permanently sealed to or separable from the body of the lid 111.

In the example system of FIGS. 1-3, a filter and/or a fluid valve and/or other feature may be positioned within or at the extending end of the lid passage 107. This filter/valve 138 may serve to create a pressure difference between the interstitial negative pressure and the negative pressure at the interior of the liner 113. Specifically, this pressure differential produces a greater negative pressure (i.e., stronger suction) in the interstitial space 200 than in the liner 113, and thereby draws the liner 113 toward the wall 112*a* of canister 112, preventing the liner 113 from collapsing as a result of the negative pressure present at its interior. The filter/valve 138 also serves to filter vapor, small solids, and other particulates from the suctioned gasses to prevent contamination of, and other damage to, downstream components, such as the canister, manifold, and vacuum pump. In some embodiments, for example, the filter may be a hydrophobic filter and/or a hydrophilic filter. An example filter usable in accordance with aspects of the present disclosure is disclosed in U.S. Pat. No. 6,780,309, which is incorporated herein by reference. The filter and/or check valve or other device may also serve as an automatic valve to close the primary suction source passageway 204 when the level of fluid collected in the liner 113 rises to the level of the filter. One suitable valve device comprises a hydrophilic material that swells when it contacts liquid to form an airtight seal that shuts off the supply of suction to the interior of the liner and prevents fluid from entering the canister and manifold passageways and thereby contaminating or otherwise damaging reusable components of the system. An example valve for closing the primary suction source usable in accordance with aspects of the present disclosure is disclosed in U.S. Pat. No. 4,384,580, which is incorporated herein by reference. Further the valve for closing the primary suction source may be a float as disclosed in U.S. Pat. No. 6,808,515, which is incorporated herein by reference. The valve may be separate from the filter or the valve and filter may be attached to each other or located in contact with each other. The filter and valve may also be integral with one another. For example, the filter/valve body may comprise a single material or composite that filters solids and particulates from gasses that are allowed to pass through the filter body until the filter/valve comes into contact with liquid, such as the collected fluids, at which time the filter/valve may close, thereby preventing the passage of fluids as well as gasses through the filter body. It will be appreciated by those skilled in the art that any equivalent system may be used to create the abovementioned pressure difference and the abovementioned aspects of the present disclosure are not limited to a filter.

The lid vacuum passageway 107 may be provided through the lid 111 and may connect to the primary vacuum passageway 204, which connects to the interstitial vacuum passageway 202 at a junction 206 provided in the body of the mounting portion 109. The manifold body auxiliary vacuum source passageway 208 may include a control valve 122 to allow manual or other control of communication of the main vacuum source with passageway portions 202, 204. The manifold body 116 and/or manifold base 114 may include a control valve receiving portion 124 (see FIG. 1(b)) for permanently or removably housing the control valve 122. The control valve receiving portion 124 may be configured to allow the control valve 122 to rotate, for example, around a rotational axis when installed into the receiving portion so as to selectively allow a passageway in the control valve 122 to enable fluid communication through the valve, or to block the passage of fluid through the control valve 122.

It will be appreciated by those skilled in the art that various alternative vacuum passageway configurations may be implemented within the scope of this disclosure. For example, various embodiments may be configured such that the interstitial vacuum passageway is routed through the canister separate from the primary vacuum passageway such that each passageway communicates with separate auxiliary vacuum source passageways of the manifold. The separate auxiliary vacuum source passageways may be independently routed to the common vacuum chamber or may join each other at an upstream junction or auxiliary vacuum chamber before reaching the common vacuum chamber. As another example, in various embodiments, the interstitial vacuum passageway may be routed independently through the canister body to a first vacuum connection at the manifold, and the primary vacuum passageway may be routed through the lid to an opening in the lid configured to connect directly to a second vacuum connection at, or separate from, the manifold.

Figure 4:
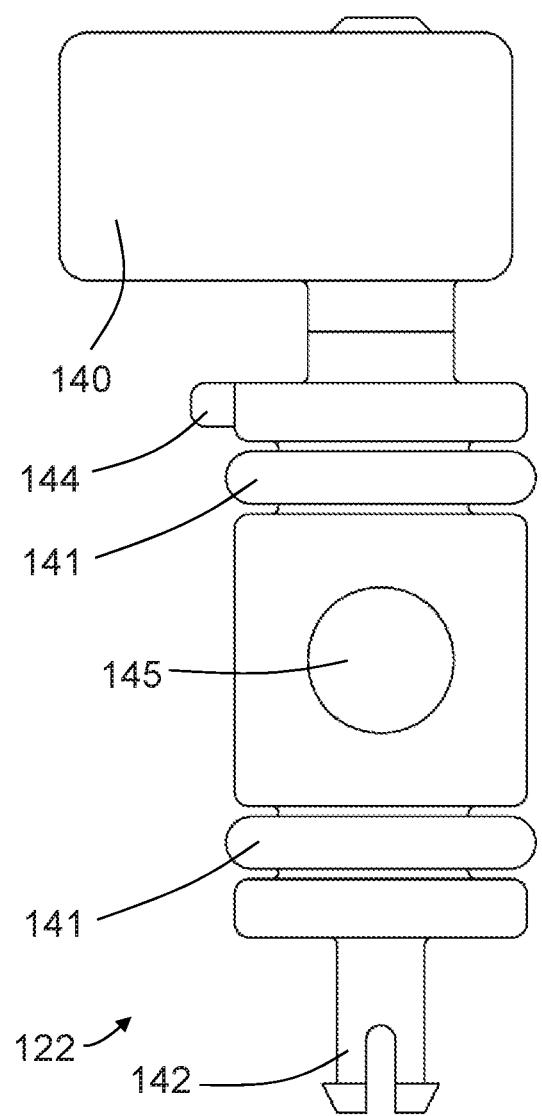
FIG. 4 illustrates an example valve that may be used to control vacuum in the manifold, according to aspects of the present disclosure.

Close-up views of an example partially assembled and fully assembled example control valve 122 in accordance with aspects of the present disclosure are illustrated in FIGS. 4(a) and 4(b). The control valve 122 may include a lever portion 140 extending from the rotational axis of the body of the valve 122. Further, the valve 122 may optionally include a single or multiple O-rings 141 to seal the space between the control valve 122 and the control valve receiving portion 124, and thereby prevent leakage of fluid or vacuum pressure from the manifold body 116 through the control valve receiving portion 124. The O-rings 141 may be formed of any suitable material capable of providing a seal when the valve 122 is assembled with the receiving portion 124. The valve 122 may further include a snap-fit portion 142 including, for example, a pair of flexible arms and ramp surfaces that engage a snap-fit receiving portion 143 within the manifold body 116. As illustrated in FIGS. 2 and 3, the snap-fit portion 142 may fit into the snap-fit receiving portion 143 in the manifold body 116 (FIGS. 2 and 3) for removably retaining the valve 122 within the manifold body 116. The valve 122 may further include a rotation stop 144 for limiting rotation along the rotational axis in either the on or off rotation position. For example, when the valve 122 is installed in the snap-fit receiving portion 143 of the manifold body 116, the valve passageway 145 may selectively be aligned with the auxiliary suction source passageway 208 (FIGS. 2 and 3). When the lever portion 140 is rotated (e.g., manually by a user), the opening 146 may be aligned or not-aligned with the auxiliary suction source passageway 208, thereby controlling communication of suction therethrough.

Figure 5:
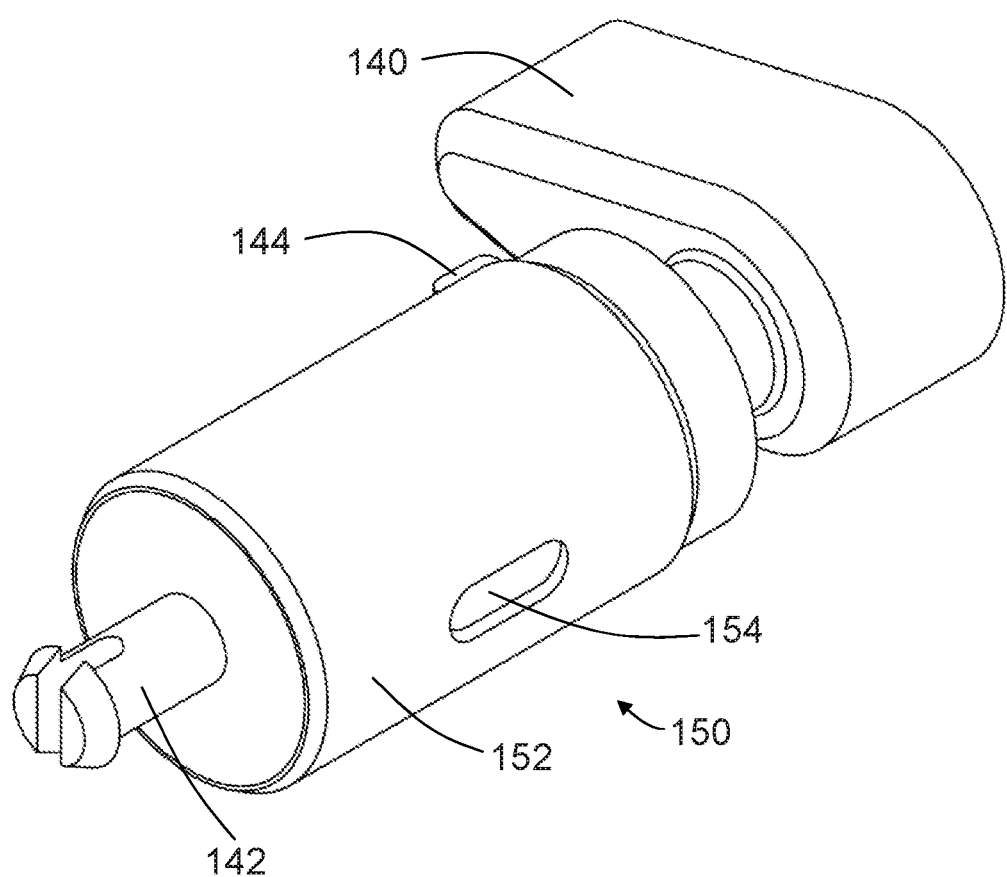
FIG. 5 is a perspective view of another example valve that may be used to control vacuum in the manifold, according to aspects of the present disclosure.

As illustrated in FIG. 5, the on/off valve 122 may also include a suitable flexible material 152 on a portion of its external surface as either an alternative to or in combination with a single or plurality of O-rings, to provide or enhance sealing when installed. Similarly to the abovementioned O-rings, the flexible material 152 may be selected to reduce leakage from the manifold body 116 at the interface between the control valve receiving portion 124 and the flexible material 152 at the outer rotational surface of the valve 150. Further the opening 154 may be formed as a narrowed slit in the lever body to increase the contact area of the seal when in the off position to reduce leakage.

Another embodiment of a fluid collection system in accordance with aspects of the present disclosure is illustrated in FIGS. 6-10. The fluid collection system 600 of this illustrated embodiment is similar in operation to the system 100 of FIGS. 1-5. It will be appreciated by skilled artisans that various features and elements as described above with respect to system 100 may be implemented with variations of the system 600 while remaining within the scope of this disclosure. In the embodiment illustrated in FIGS. 6-10, each canister assembly 601 has a lid 611, which may include a liner 613, similar to the liner 113 illustrated in FIG. 1(b) and described above, or may receive fluids directly into the canister 612. The lid 611 forms a seal with the canister body 612. The canister body 612 and lid 611 may be configured to be attached using, for example, an interference fit, a threaded canister body and corresponding threaded lid, tabs for creating a connection between the canister and lid, and/or any other method or features allowing a similar positive connection between the lid and canister. The canister body or lid may include visual indicia to indicate that a positive connection is completed between the canister body and lid. Audible and tactile indicia may also be used, for example, the lid may include tabs that produce a click or snap that may be heard and/or felt by the user when a positive connection is made. Each lid 611 may include a lid vacuum passageway cap 608 similar in function to the cap 108 of the system of FIGS. 1-5, and each lid 611 may also include a pivotally mounted handle 602. Alternatively, the handle 602 may be a molded portion of the lid or may be attached in any suitable manner to the lid or the canister body.

Figure 6:
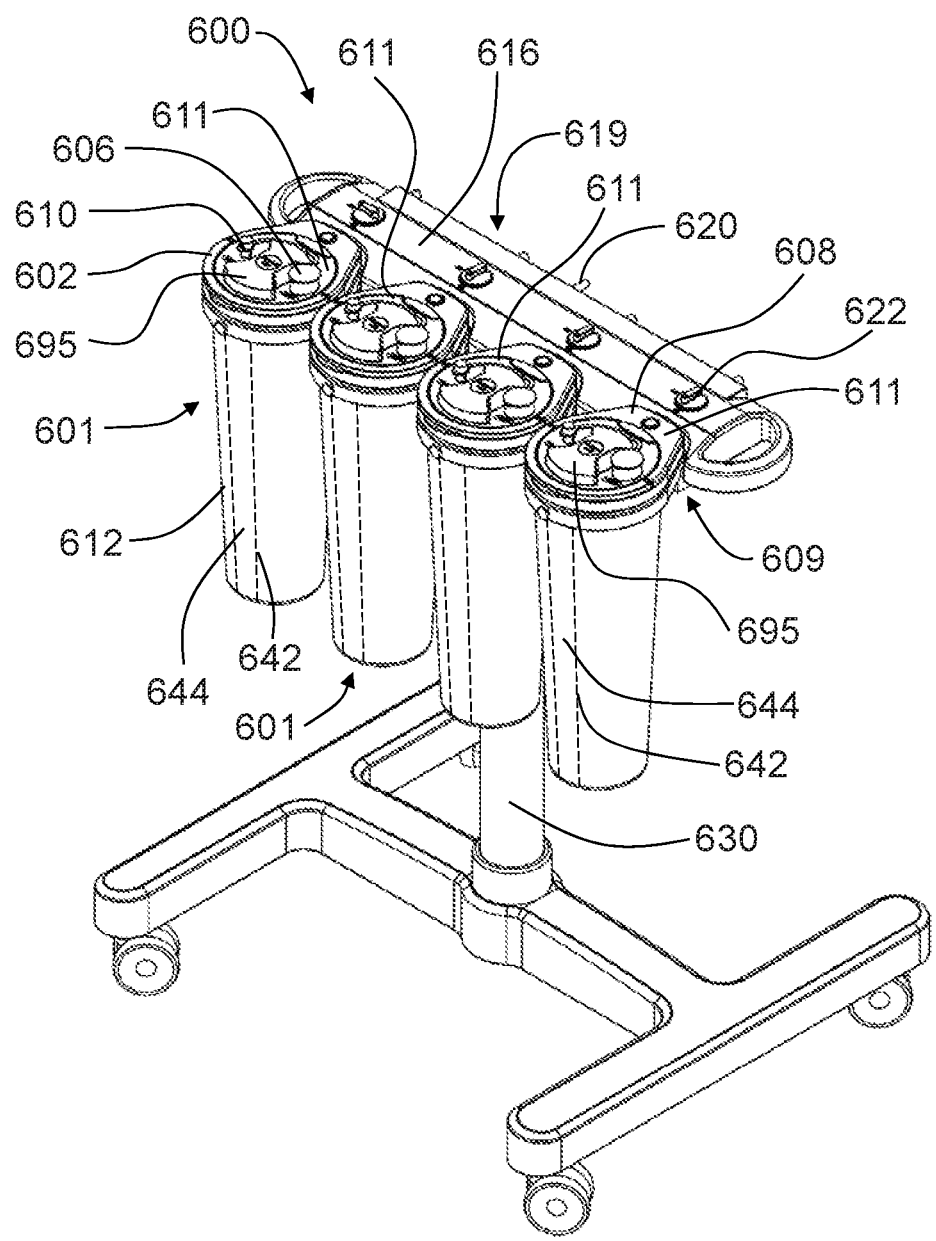
FIG. 6 is a perspective view of another example fluid collection system including multiple suction canister assemblies linearly mounted to corresponding mounting interfaces of a manifold body, in accordance with aspects of the present disclosure.
Figure 7:
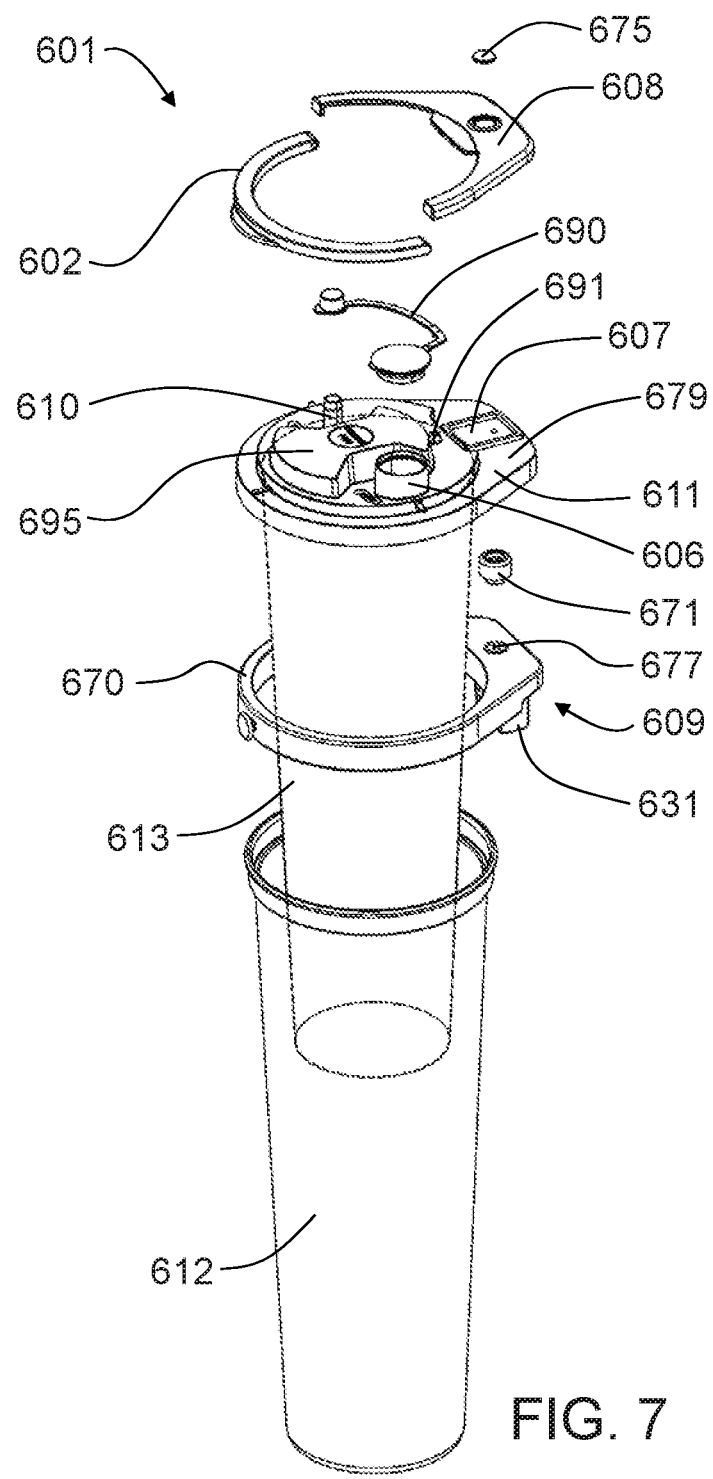
FIG. 7 is an exploded view of a canister assembly in accordance with aspects of the present disclosure.
Figure 8:
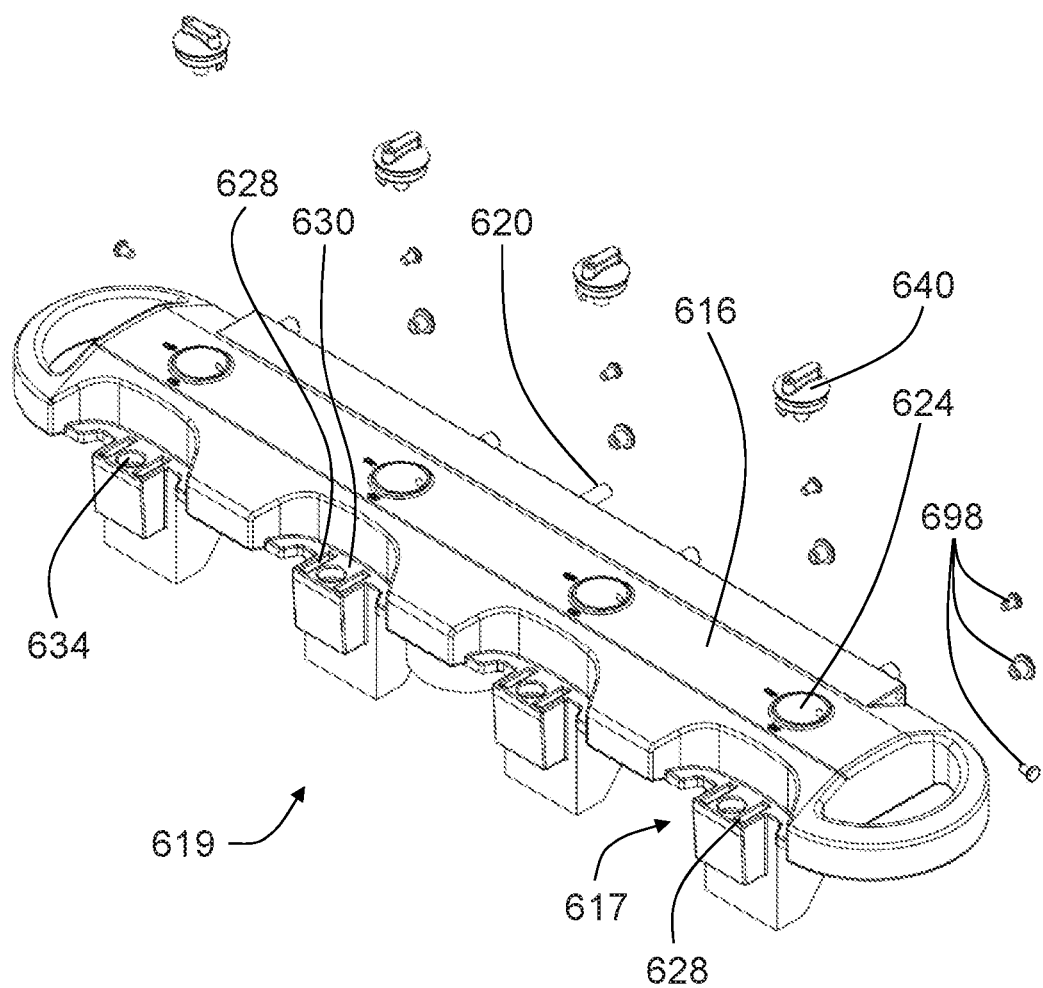
FIG. 8 is an exploded view of a manifold assembly in accordance with aspects of the present disclosure.
Figure 9:
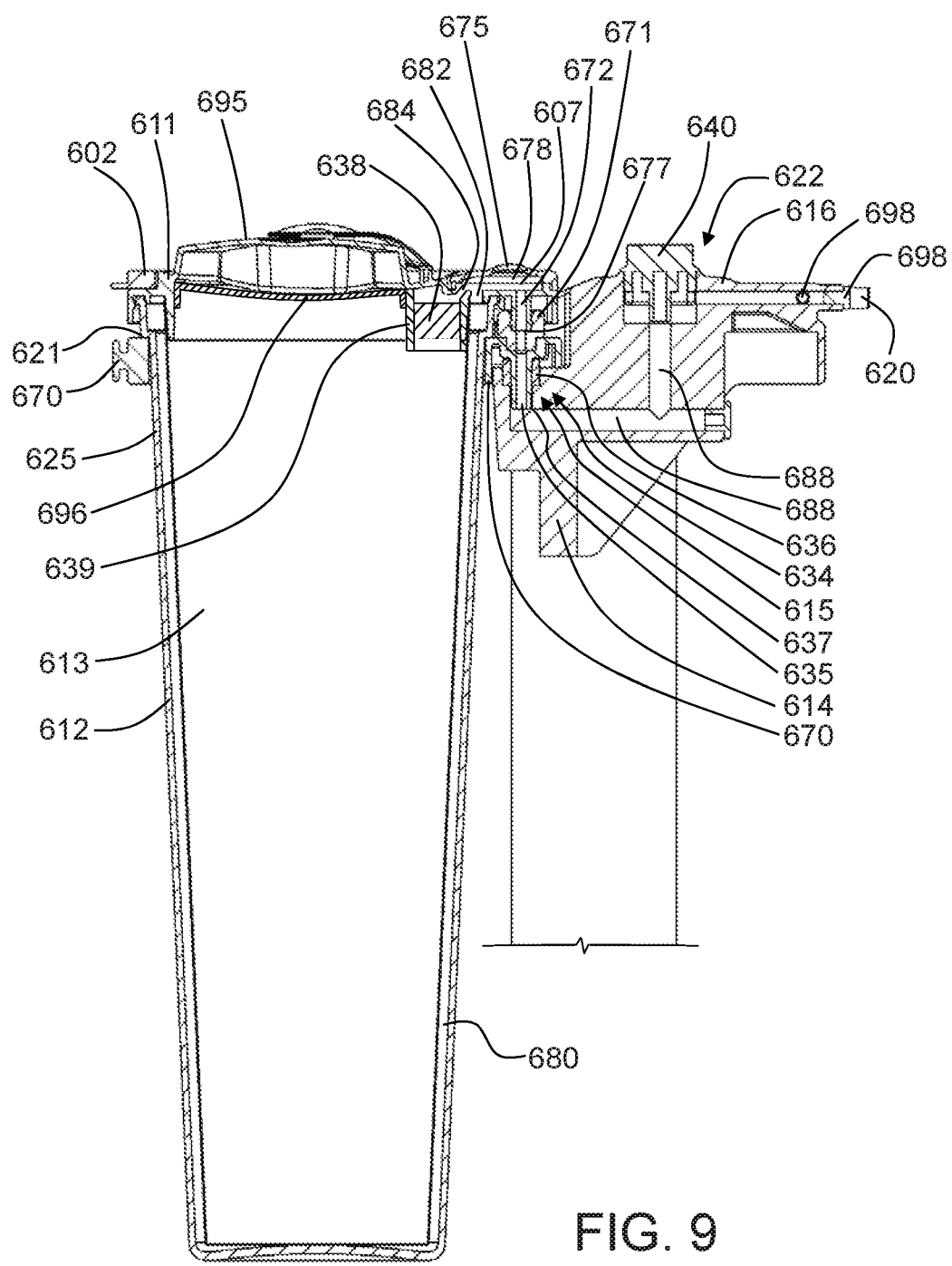
FIG. 9 is a sectional view of the example fluid collection system of FIG. 6, including a canister assembly mounted to the manifold, according aspects of the present disclosure.

In this example system 600, the canister body 612 is configured to be inserted into a ring holder 670 mountable to a manifold 619 such that the canister 612 is supported by the ring holder 670. For example, as illustrated in FIG. 9, the ring holder 670 abuts against a shoulder 621 of the canister 612 near its open end and/or against the canister wall 625 about its circumference, thereby firmly holding the canister 612 in relation to the ring holder 670. The ring holder 670 has a protruding mounting portion 609 configured to mate with a ring holder receiving portion 617 of the manifold body 616. A connector portion 635 and elongated guide members 631 extend from the protruding mounting portion 609 of the ring holder 670. Connector receiving portion 634 and guide slots 628 provided at the ring holder receiving portion 617 are configured to mate with the connector portion 635 and guide members 631 of the ring holder 670, respectively, to securely hold the ring holder 670 relative to the manifold body 616. The manifold body 616 may optionally be mounted to a manifold base 614, which may be either permanently mounted to a surface or a mobile support (e.g., on wheels or feet), such as a rolling stand 630, as illustrated in FIG. 6. The lid 611 and/or canister body 612 may be keyed or include a protrusion corresponding to a receiving portion of the ring holder 670 and/or the ring holder receiving portion 617, for example, so that the canister and/or lid can only be mounted in a single orientation or limited selection of orientations relative to the manifold 619.

Figure 10:
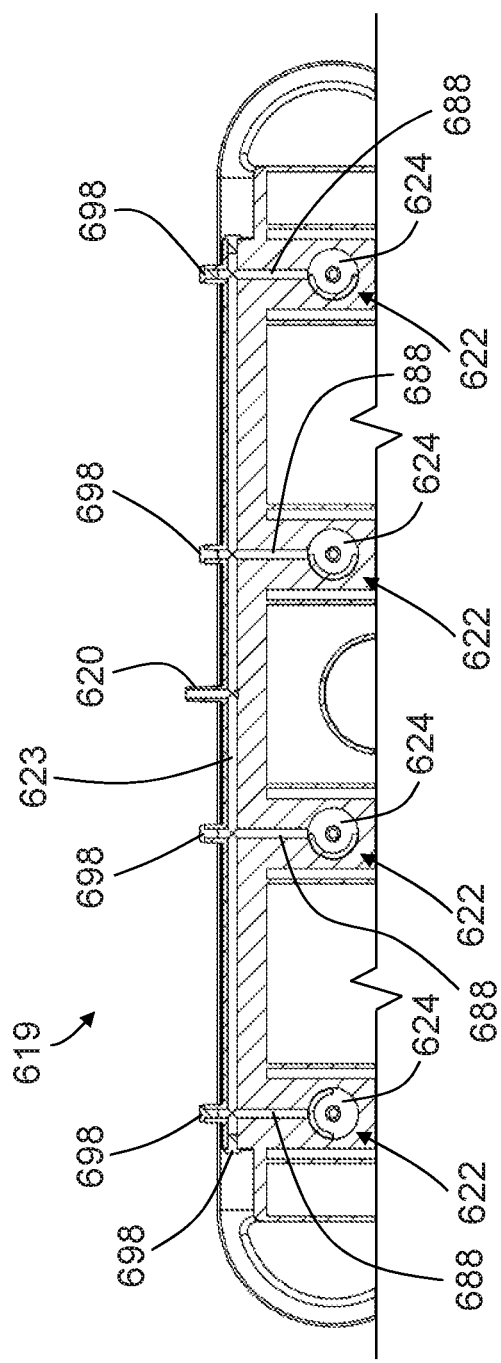
FIG. 10 is a sectional view of the manifold of the example fluid collection system of FIG. 6 according aspects of the present disclosure.
Figure 11:
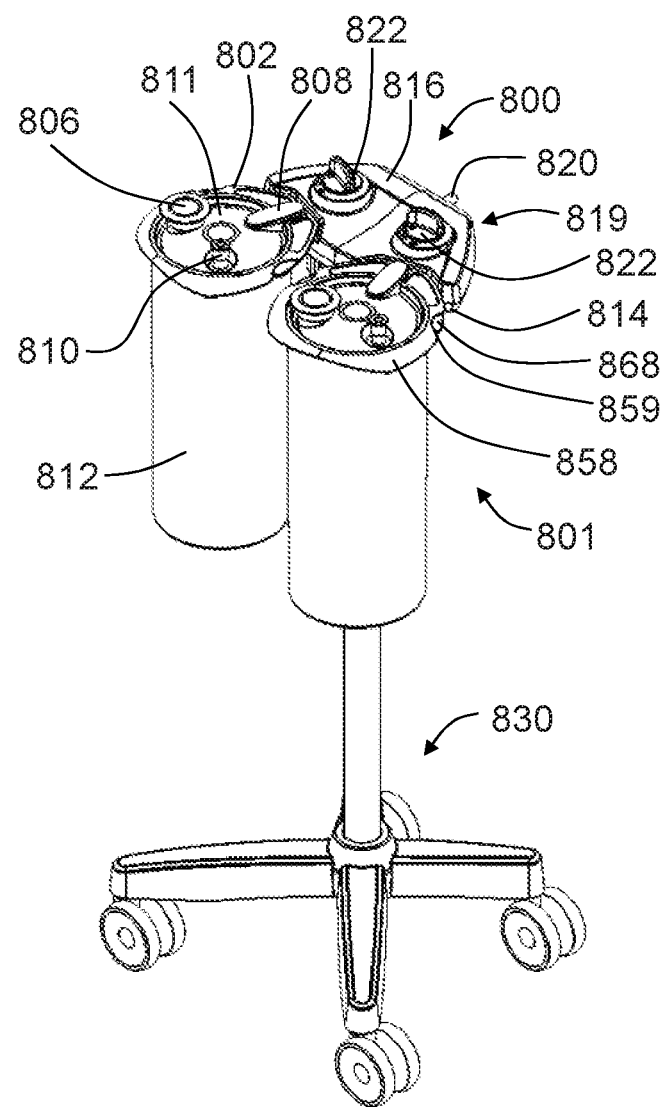
FIG. 11 is a perspective view of another example fluid collection system.
Figure 12:
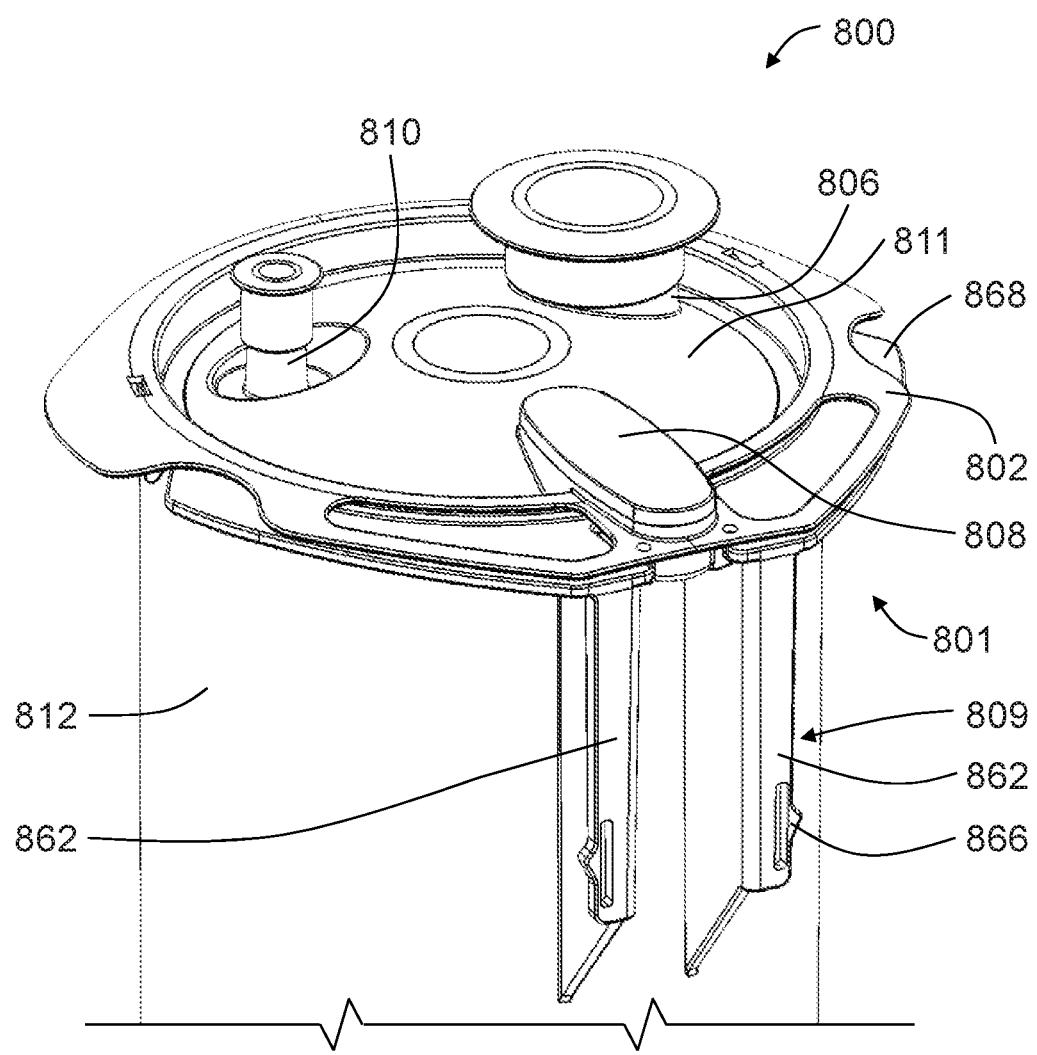
FIG. 12 is a detail view of a canister assembly in accordance with aspects of the present disclosure.

The manifold 619 may receive vacuum pressure from a main vacuum source, such as a central vacuum source of a healthcare facility, via vacuum source connector 620, or may have a vacuum pump contained directly in or attached to the manifold. Similarly to the manifold 119 illustrated and described with regard to FIGS. 1-5, the main vacuum source may be connected to a common vacuum chamber or, as illustrated in FIG. 10, a common vacuum source passageway 623, and may be divided into a single or plurality of auxiliary vacuum source passageways 688 leading to one or more auxiliary vacuum source connector openings 637. For manufacturing simplicity, the passageways 623, 688 may be drilled through the manifold body 616 and sealed at various openings by plugs 698. One or more of the common vacuum source passageway 623 and auxiliary vacuum source passageways 688 may include one or more user-controllable valves 622. Each valve 622 may include a valve body 641 that is received in a valve receiving portion 624 of the manifold 619. Each valve body 641 may be rotated using knob portion 640 to shut off vacuum supply from the main vacuum source or to individual auxiliary vacuum source connectors. The ring holder connector portion 635 and/or auxiliary vacuum source connector 615 may include a single or plurality of seals for enhancing the seal of the interface between the connector 635 and the auxiliary vacuum source connector 615.

Each lid 611 may further include a vacuum source connector portion such as, for example, the nozzle 672 illustrated in FIG. 9. When a user places the canister assembly 601 into a ring holder 670 mounted to the manifold body 616, the opening of the nozzle 672 interfaces with an opening 677 in the ring holder 670, which is in communication with the auxiliary vacuum source passageway 688, such that a vacuum supply may be communicated with the canister assembly 601. A nozzle seal 671 may be provided between the nozzle 672 and the ring holder 670 to enhance the seal of the connection.

In the embodiment of FIGS. 6 to 10, vacuum supplied to the lid vacuum passageway 607 via nozzle 672 is routed through lid vacuum chamber 678 and to the interior of the liner 613 via liner vacuum passageway 684, and to the interstitial space 680 via interstitial vacuum passageway 682. Each lid 611 may further include a patient port 610 and/or tandem port 606, and may optionally include an accessory port (not shown) similar to accessory port 104 shown in FIGS. 1-3. Port caps 690 are tethered to each other and attached to an anchor 691 integrally molded with the lid 611. Port caps may also be integrally molded with the lid or provided separately from the lid, and they may be attached to the lid by various means as will be appreciated by those skilled in the art; for example, they may be attached with adhesives, welded, tied, or attached by other similar means.

In this embodiment, a portion of the lid vacuum passageway cap 608 is configured as a vacuum bulb 675 to indicate the presence of negative pressure in the lid vacuum chamber 678. The vacuum bulb 675 may be a dome-shaped wall section that may be formed of a material that is more elastic than adjacent wall portions of the cap 608 and/or it may have a thinner wall thickness than surrounding wall portions. When negative pressure in the lid vacuum chamber 678 reaches a desired threshold, the vacuum bulb dome may invert, thereby providing visual and/or audible indication that vacuum is supplied to the canister assembly 601. When the suction supply to the canister assembly 601 is shut off, the dome of the vacuum bulb 675 may revert to its original state, thereby indicating that suction supply to the canister is shut off. The vacuum bulb 675 may be molded integrally with the cap 608 from the same material or it may be formed of a different material that may be overmolded, adhered, welded, or otherwise sealingly affixed to the cap 608.

A filter/valve 638 similar to the filter/valve 138 described above with respect to system 100 is positioned between the liner vacuum passageway 684 and the interior of the liner 613 to provide the abovementioned pressure differential between the interior of the liner 613 and the interstitial space 680, and to serve as a filter for suctioned gasses and/or shutoff valve for shutting off suction supplied to the canister when collected fluids contact the filter 638. In the embodiment of FIGS. 6-10, the filter/valve 638 is positioned within a filter/valve housing 639 at an end of the liner vacuum passageway facing the interior of the liner 613. Further, it will be appreciated by those skilled in the art that many of the features disclosed herein may also be implemented in connection with canister systems that lack a liner such that fluid is collected directly in the canister itself.

As illustrated in FIGS. 6-9, the lid 611 of this embodiment includes a dome portion 695 that defines a recess at the underside of the lid 611 for storing a treatment agent (not shown) such as a solidifying and/or a disinfecting agent. Powdered or granulated solidifying or disinfecting agents, for example, are commonly added to collected fluids to prevent splashing or spillage and reduce the risk of contaminating personnel during transport and disposal of waste fluids collected in the liner or directly in the canister itself. Such treatment agents may be stored in recess of the dome portion 695, which may then be sealed by, for example, a foil or film seal 696 which may be sealed with adhesives, heat, sonic welding, or other suitable sealing methods and mechanisms. When desired, such as after a surgical procedure or after the liner or canister is filled with collected fluid, a user may depress the top of the dome portion 695, which may cause the dome portion 695 to collapse, partially collapse, or invert and thereby exert sufficient pressure on the contents of the dome portion 695 to rupture or otherwise break the seal 696, thereby releasing the contents into the collected fluids. This feature allows collected fluids to be sanitized and/or solidified without the need to open a port or otherwise provide direct access to the waste fluid to pour in treatment agents or attach a separate container of treatment agents. It will be appreciated that a variety of structures are suitable for providing a space at a portion of the lid facing the interior of the liner and/or canister for housing treatment agents and which are sufficiently flexible to at least partially collapse as a result of a force exerted at the upward-facing side of the lid. It will also be appreciated by those skilled in the art that a variety of seal structures in addition to foil or film seals may be implemented within the scope of this disclosure. As one non-limiting example, a cap or a plug may attach via an interference fit, friction fit, and/or snap-fit to a receiving portion at the underside of the lid such that pressure exerted on the contents by flexure or at least partial collapse of the dome portion may dislodge or rupture the cap or plug, thereby releasing the contents into the collected fluids.

The canister body 612 and/or the liner 613 may include markings 642 (FIG. 6) for indicating a volume of fluids contained in the canister. The canister body 612 may further include a writable portion 644 which may be shrink-wrapped around the canister, permanently printed or molded to the canister, or may be in the form of a removable strip. In various embodiments, the liner includes volume markings readable through the canister during use. The manifold and/or mounting brackets may also include a storage portion. It will be appreciated by those skilled in the art that a storage portion could be formed as, for example, a hook, a shelf, a drawer, a cabinet, a container, or any other device suitable for storing, holding, or retaining accessories.

An alternative embodiment of a fluid collection system in accordance with aspects of the present disclosure is illustrated in FIGS. 11-22. The fluid collection system 800 of this illustrated embodiment is similar in configuration and operation to the system 100 of FIGS. 1-5 and the system 600 of FIGS. 6-10. It will be appreciated by skilled artisans that various features and elements as described above with respect to system 100 and system 600 may be implemented with variations of the system 800 while remaining within the scope of this disclosure. In the embodiment illustrated in FIGS. 11-22, the system 800 includes a vacuum manifold 819 mounted at an upper end of a rolling stand 830. One or more canister assemblies 801 may be mounted to the manifold 819 and supported in a desired position and orientation by the manifold body 816, manifold base 814, and/or roll stand 815.

Each canister assembly 801 includes a canister 812 having an opening 818 (FIG. 13) and a lid 811, which may include an attached liner 813, similar to the liner 113 illustrated in FIG. 1(b) and described above, or may receive fluids directly in the canister 812. The lid 811 includes a patient port 810 and an accessory or tandem port 806. In various embodiments, one or more additional ports or connections of varying sizes and configurations may be included to, for example, connect additional suction instruments or tubing, connect to other canister assemblies, facilitate drainage or evacuation of fluids collected in the liner or canister, introduce solidifying and disinfecting agents, provide access to collected fluids for sampling and measuring, and/or connect various accessories such as a solids filter or smoke filter. Each lid 811 may include a lid vacuum passageway cap 808 similar in function to the cap 108 of the system of FIGS. 1-5, and each lid 811 may also include one or more integrally molded handles 802. Alternatively, one or more handles may be pivotally mounted or attached in any suitable manner to the lid and/or the canister body.

Figure 13:
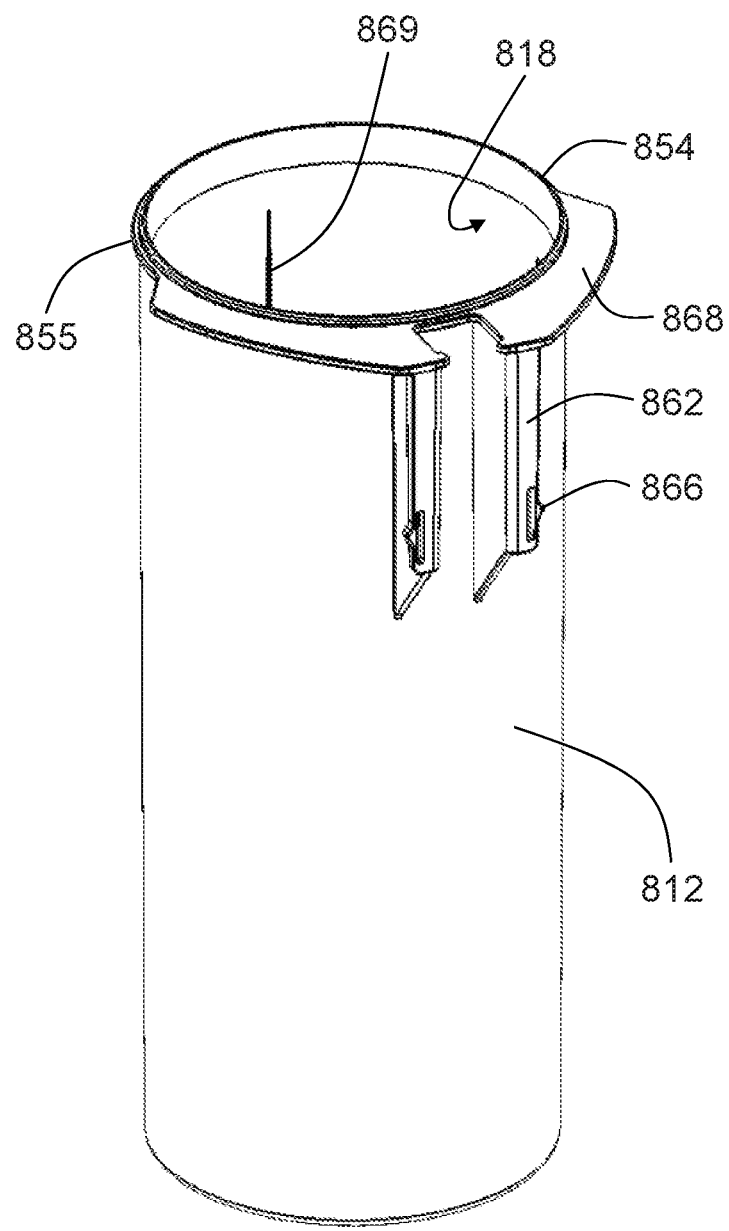
FIG. 13 is a perspective view of a canister in accordance with aspects of the present disclosure.
Figure 14:
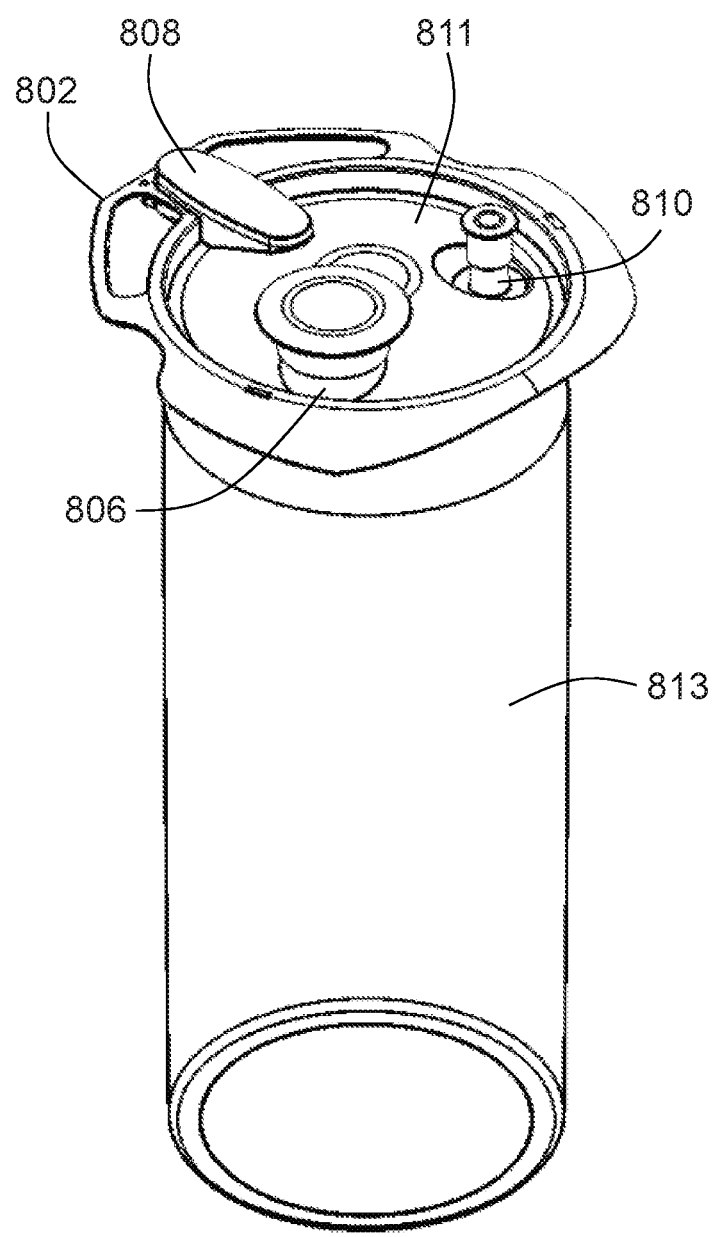
FIG. 14 is a perspective view of a lid and liner assembly in accordance with aspects of the present disclosure.
Figure 15:
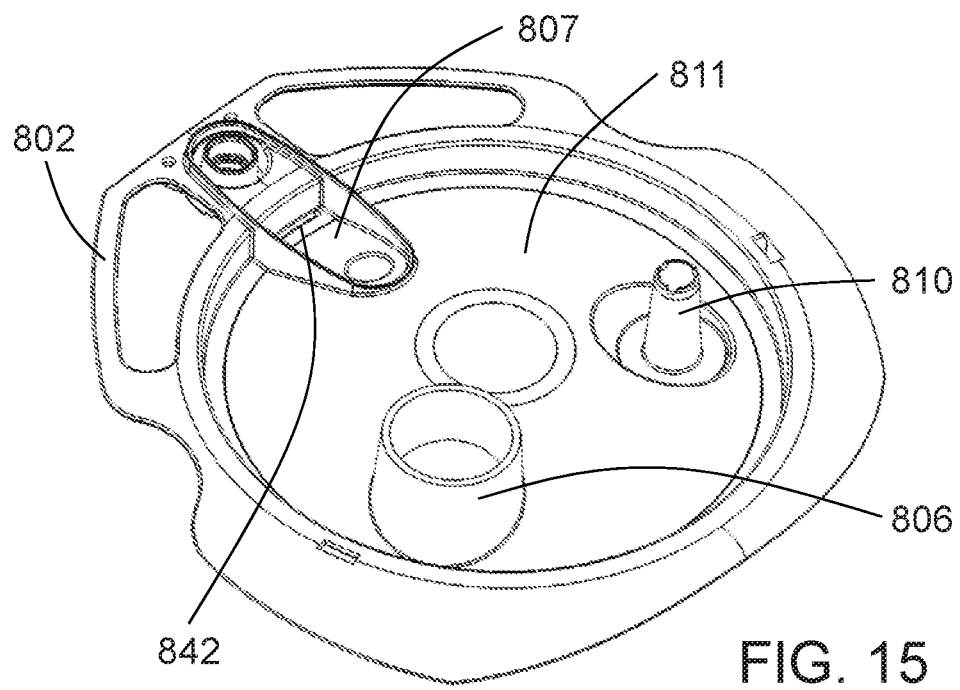
FIG. 15 is a perspective view of a lid in accordance with aspects of the present disclosure.
Figure 16:
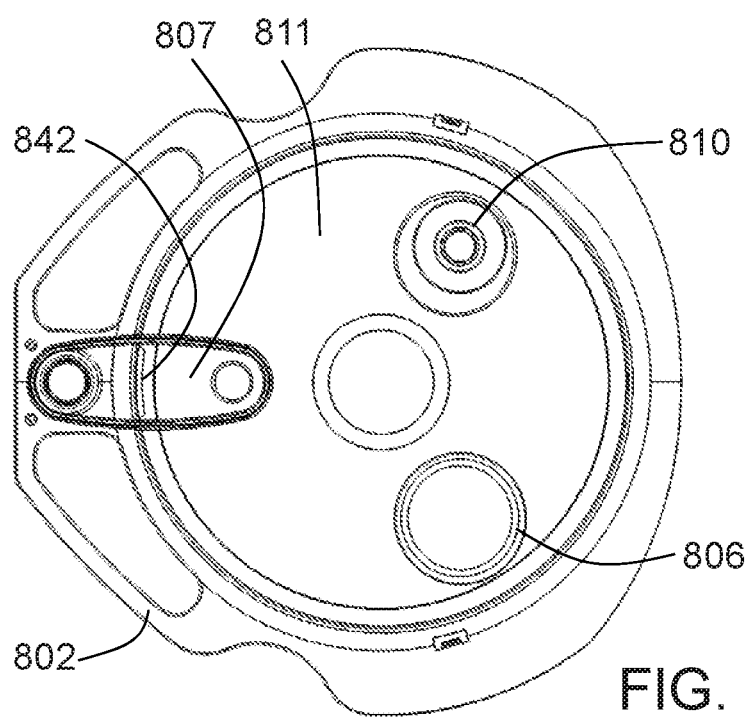
FIG. 16 is a top view of a lid in accordance with aspects of the present disclosure.
Figure 17:
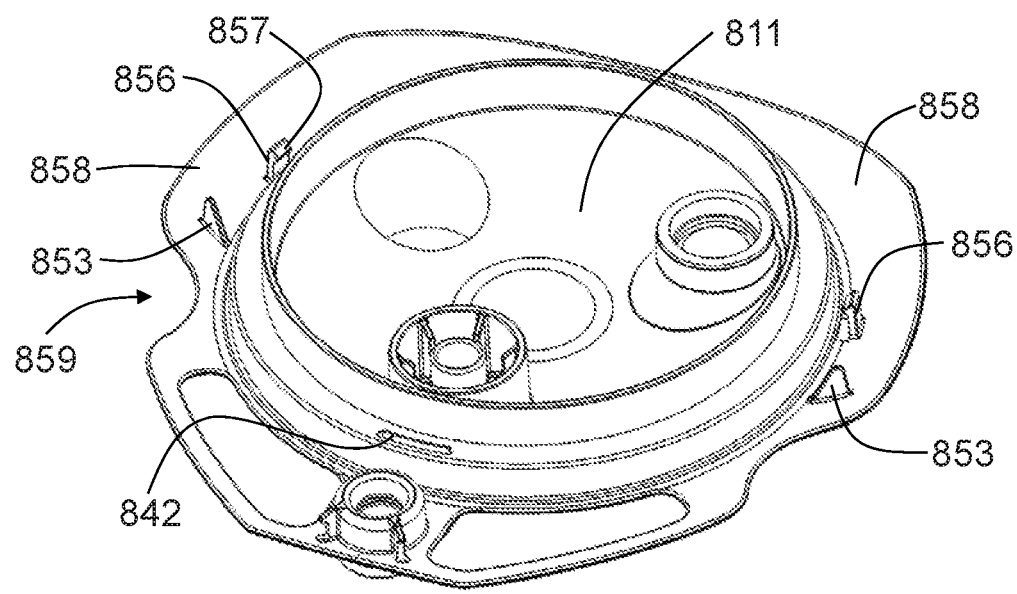
FIG. 17 is a bottom perspective view of a lid in accordance with aspects of the present disclosure.
Figure 18:
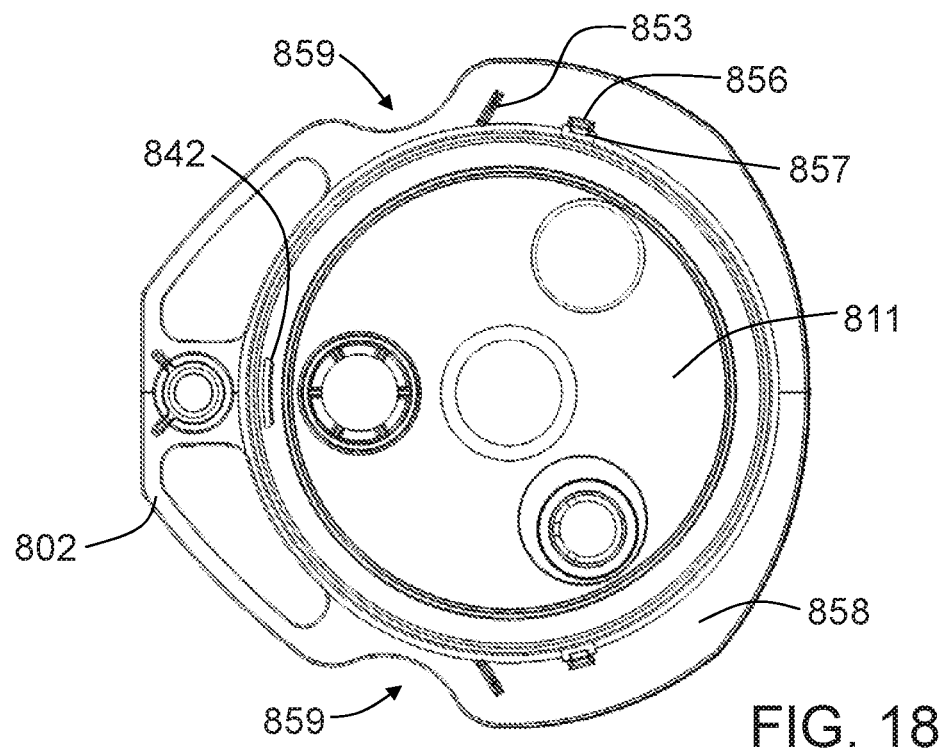
FIG. 18 is a bottom view of a lid in accordance with aspects of the present disclosure.
Figure 19:
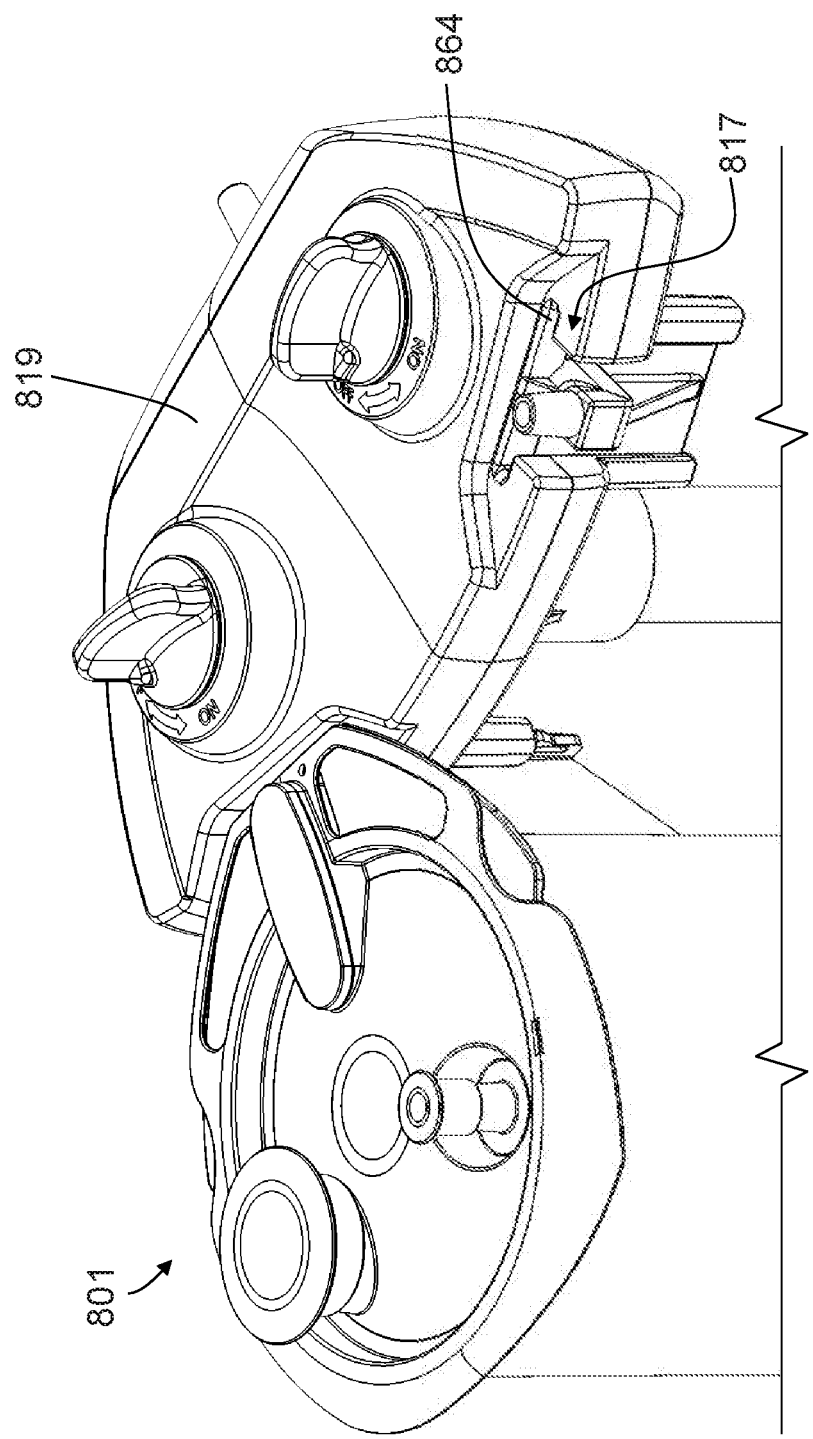
FIG. 19 is a detail perspective view of a fluid collection system in accordance with aspects of the present disclosure.

In this embodiment, the lid 811 forms a seal with the canister body 812 using an interference fit between an annular wall 852 of the lid 811 and a lip 854 of the canister body 812 (FIGS. 13 and 17). Additionally, the lid 811 is secured with tabs 856 to a rim 855 of the canister body 812. Each tab 856 includes a ramped protrusion 857 that engages the rim 855 as the lid 811 is lowered over the canister opening 818, causing the tabs 856 to deflect outward. When the ramped protrusion 857 clears the lower edge of the rim 855, the tabs 856 retract inward, which positions the ramped protrusion 857 underneath the bottom edge of the rim 855 and results in a positive locking connection between the lid 811 and the canister body 812. The tabs 856 also provide an audible and tactile "click" as they snap into place, indicating to the user that the lid is properly seated and locked to the canister. In various embodiments, the canister body and lid may be configured to be attached using, for example, an interference fit, a threaded canister body and corresponding threaded lid, removable or permanent adhesive/sealant, deflectable or deformable tabs for creating a positive mechanical connection between the canister and lid, and/or any other method or features for providing a sealing engagement between the lid and canister. The canister body or lid may include visual, audible, and/or tactile indicia to indicate that a positive connection is established between the canister body and lid.

In this example system 800, the canister body 812 includes a mounting portion 809 including an opposing pair of mounting rails 862 configured to mate with corresponding mounting slots 864 provided at a canister receiving portion 817 of the vacuum manifold 819 to support the canister 812 in an upright orientation. Retention tabs 866 are configured to assist in retaining the canister 812 in the canister receiving portion 817 by providing additional resistance to removal of the canister 812. Alternatively, releasable locking features, such as a spring-biased pin and slot mechanism, resistance mechanisms, such as interference and friction-enhancing fits, or any suitable method or mechanism may be employed to help retain the canister body in a stable, mounted position on the manifold and to help prevent accidental or unintended removal of the canister. The canister 812 includes flanges 868 that facilitate handling of the canister during installation and removal and provide a stop for limiting motion of the canister 812 via contact with a transverse surface of the manifold body 816 when the canister is mounted to the manifold 819. Canister flanges 868 may also assist with removal of the lid 811 from the canister 812. The lid 811 includes lid flanges 858 that may be gripped by a user such that the ends of a user's fingers grip the underside of the lid flanges 858. The lid flanges 858 include recesses 859 that expose portions of the upper surfaces of the canister flanges 868 when the lid 811 is installed on the canister 812. A user, while gripping the underside of the lid flanges 858 with the ends of his or her fingers, may simultaneously press downward on the exposed portions of the canister flanges 868 with his or her thumbs to provide leverage while lifting the lid 811. The upward force applied to the lid flanges 858 also causes the tabs 856 to flex radially outward, thereby moving the ramped protrusions 857 out from the underside of the rim 855 and allowing the lid 811 to be lifted and removed from the canister 812. Additionally, the canister 812 may include ribs 869 along the interior wall of the canister 812 to provide additional strength and rigidity, and to facilitate removal of the lid/liner by reducing friction between the liner and the canister wall and by providing passages for ambient or atmospheric pressure to relieve vacuum pressure that may otherwise accumulate and become sealed between the liner and the canister walls during use.

Figure 20:
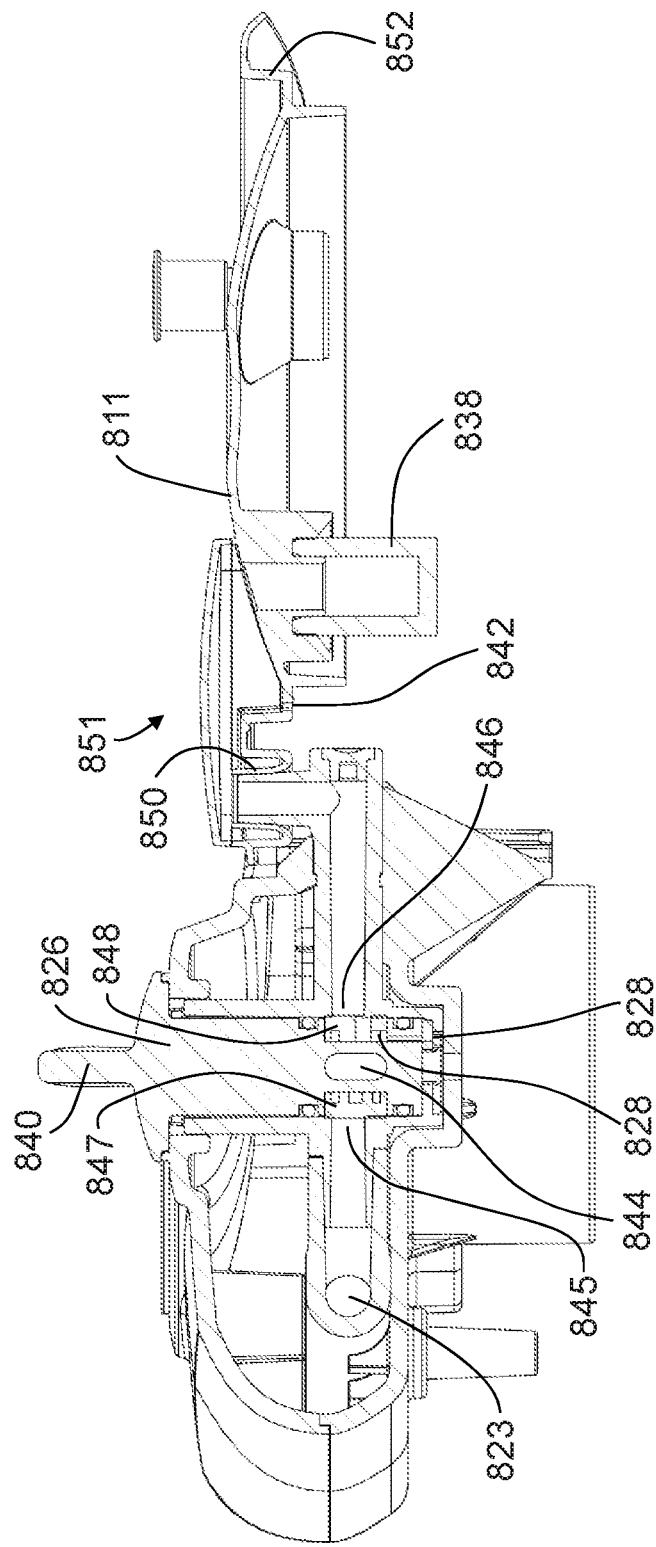
FIG. 20 is a cross-sectional view of a fluid collection system in accordance with aspects of the present disclosure.
Figure 23:
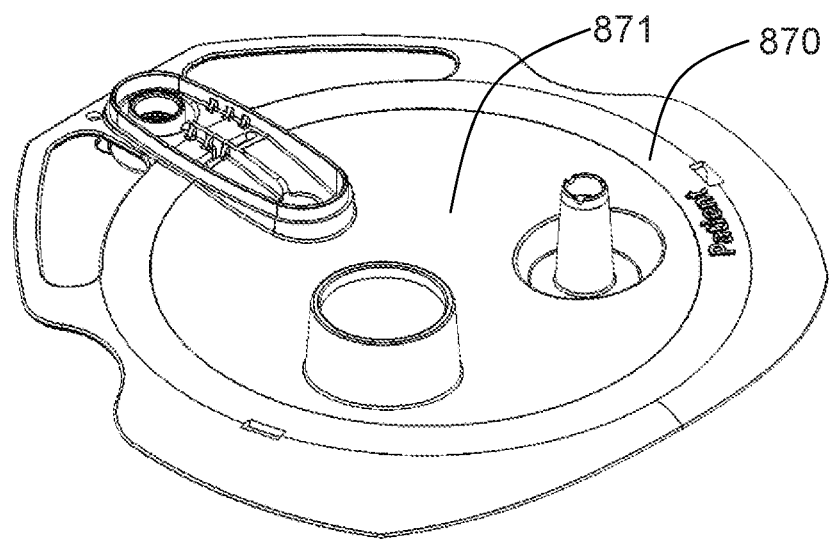
FIG. 23 is a perspective view of a lid in accordance with aspects of the present disclosure.
Figure 24:
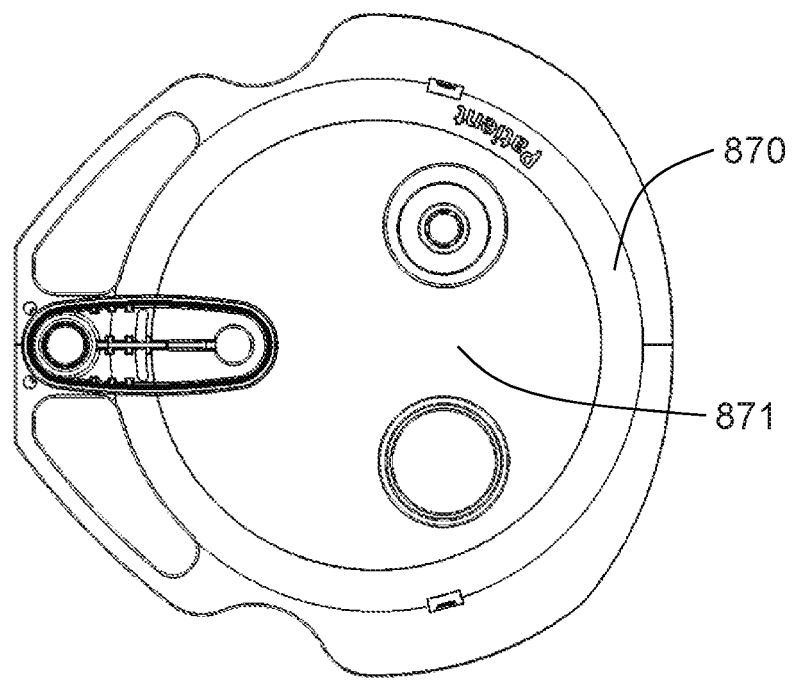
FIG. 24 is a top view of a lid in accordance with aspects of the present disclosure.
Figure 25:
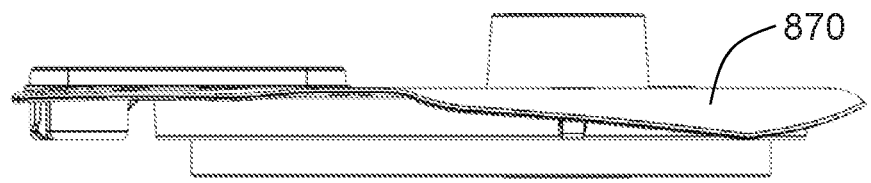
FIG. 25 is a side view of a lid in accordance with aspects of the present disclosure.
Figure 26:
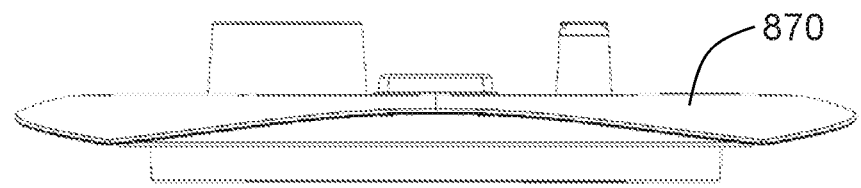
FIG. 26 is a front view of a lid in accordance with aspects of the present disclosure.

Referring to FIG. 20, the lid 812 defines a lid vacuum passageway 807 that communicates vacuum between the interior of the liner 813 and a lid vacuum port 850. The lid vacuum passageway 807 extends through a protrusion 851 that extends radially outward in a horizontal plane beyond the outer perimeter of the canister opening 818 when the lid 811 is mounted to the canister body 812. The lid vacuum port 850 is provided at a distal portion of the protrusion 851 as shown in FIG. 17. An interstitial vacuum passageway 842 in the lid 811 communicates vacuum present in the lid vacuum passageway 807 with the interstitial space 880. A lid vacuum passageway cap 808 may be removably or permanently sealed to the lid by, for example, laser, heat, friction, or ultrasonic weld, adhesives, interference or snap fit, or by using any other suitable method and features. Alternatively, the lid vacuum passageway cap 808 may be integrally molded with the lid 811 such that a separate lid vacuum passageway cap piece is not necessary. A filter and/or fluid shutoff valve 838 is provided between an end of the lid vacuum passageway 807 and the interior of the liner 813. Alternatively, the filter and/or shutoff valve may be positioned within the lid vacuum passageway or at any location along the vacuum path between the interior of the liner and the interstitial vacuum passageway. In various other embodiments, the filter and/or shutoff valve may be positioned at any location along the vacuum path between the interstitial space and the lid vacuum passageway and at any location along the vacuum path between the manifold and the interior of the liner.

As illustrated in FIG. 20, the lid vacuum port 850 is configured to mate with an auxiliary vacuum source connector 815 provided at the manifold 819. To facilitate installation of the lid 811 onto the canister 812, guide members 853 (FIG. 17) extending from the underside of the lid 811 may contact the canister 812 and guide the lid into proper alignment as the user lowers the lid onto the canister 812. The lid 811 and/or canister body 812 may be keyed or include a protrusion matching a receiving portion of the canister 812 and/or the manifold 819, for example, so that the canister and/or lid can only be mounted in a single orientation or limited selection of orientations. In various embodiments, visual and/or tactile indicia may be provided on the canister, lid, and/or manifold to indicate proper orientation and alignment of the lid relative to the canister and/or manifold. The auxiliary vacuum source connector 835 and/or lid vacuum port 850 may include a single or plurality of seals, for example O-ring seals, for enhancing the seal of the interface between the auxiliary vacuum source connector 835 and the lid vacuum port 850.

The manifold 819 may receive vacuum pressure from a main vacuum source line via main vacuum source connector 820. Alternatively, a vacuum pump or other vacuum supply may be contained directly in or attached to the manifold. Similar to the manifold 119 illustrated and described with regard to FIGS. 1-5, the main vacuum source may be connected to a common vacuum chamber or, as illustrated in FIG. 20, a common vacuum source passageway 823, which may be divided into a single or plurality of auxiliary vacuum source passageways 888 leading to one or more auxiliary vacuum source connectors 815. In this embodiment, the common vacuum source passageway 823 and auxiliary vacuum source passageways 888 are defined by a central manifold piece 882 that is molded separately from the manifold body 816 and manifold base 814. Alternatively, the auxiliary vacuum source passageways 888 may be drilled or machined after molding, or they may be integrally molded with the manifold body and/or manifold base, similar to the manifold 619 of FIGS. 6-10.

One or more of the common vacuum source passageway 823 and auxiliary vacuum source passageways 888 may include one or more valves 822 user-controllable by, for example, knobs 840 for shutting off vacuum communication from the main vacuum source or to each auxiliary vacuum source connector 815 independently. For example, in the embodiment of FIGS. 11-22, the valve 822 is positioned along the auxiliary vacuum source passageway 888 such that when the valve 822 is in an open position, a valve passageway 844 is aligned with upstream and downstream openings 845, 846 of the auxiliary vacuum source passageway 888 such that vacuum may be communicated between the common vacuum source passageway 823 and the auxiliary vacuum source connector 815. When the valve 822 is rotated to a closed position, seal pads 847, 848 close the openings 845, 846 to prevent communication of vacuum between the common vacuum source passageway 823 and the portion 889 of the auxiliary vacuum source passageway 888 that is downstream of the valve 822.

If the downstream opening 846 is fully sealed when the valve 822 is rotated to the closed position, vacuum that has accumulated in the interstitial space 880 during use could make removal of the lid 811 from the canister 812 difficult as a result of the pressure differential between the interstitial space 880 and atmosphere. Furthermore, fluid collected in the liner 813 could potentially reflux as a result of abrupt pressure changes in the interstitial space 880 and/or the interior of the liner 813. To avoid these complications, the valve 822 includes a relief vent 828 configured to allow atmospheric pressure to enter into the downstream portion 889 of the auxiliary vacuum source passageway 888 (and consequently into the interstitial space 880 and/or the interior of the liner 813 via lid vacuum passageway 807) at a predetermined rate when the valve 822 is in the closed position. When the venting seal pad 848 covers the downstream opening 846 (i.e., when the valve 822 is in the closed position), atmospheric pressure is allowed to enter the downstream portion 889 of the auxiliary vacuum passageway 888 via passageways 862, 864 provided through the valve body 826 and the venting seal pad 848 and an opening (not shown) in the manifold base 814. It will be appreciated by persons of ordinary skill in the art that venting to atmosphere may be accomplished through various alternative passageway routings or other features or configurations designed to communicate the interstitial space and/or the interior of the liner with atmosphere.

Figure 27:
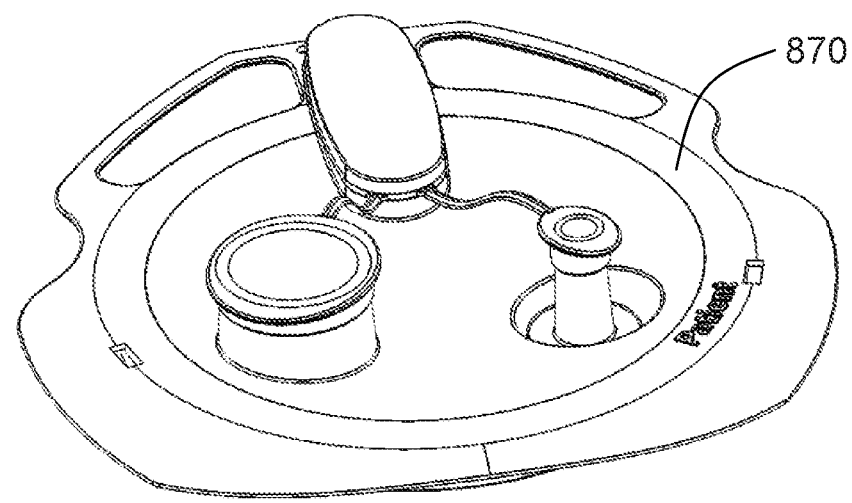
FIG. 27 is a perspective view of a lid assembly in accordance with aspects of the present disclosure.
Figure 28:
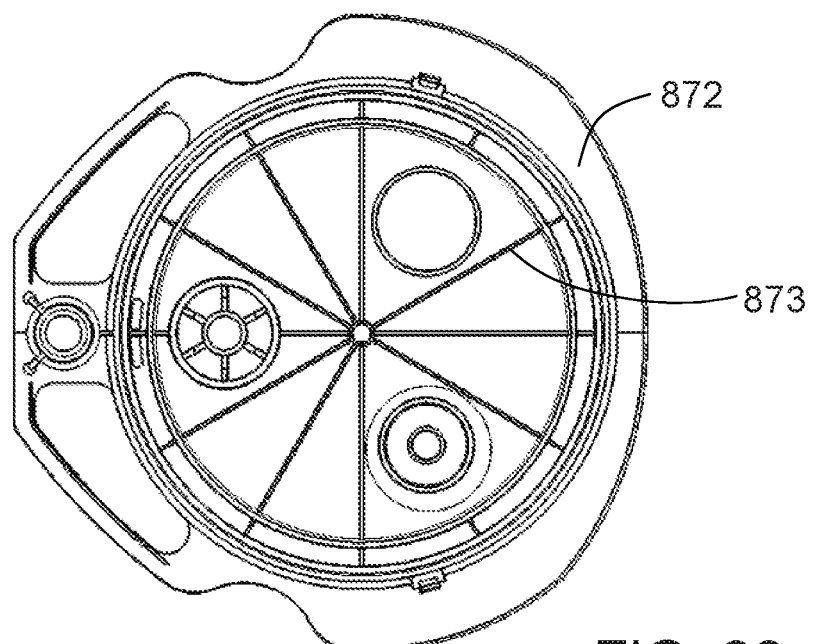
FIG. 28 is a bottom view of a lid in accordance with aspects of the present disclosure.
Figure 29:
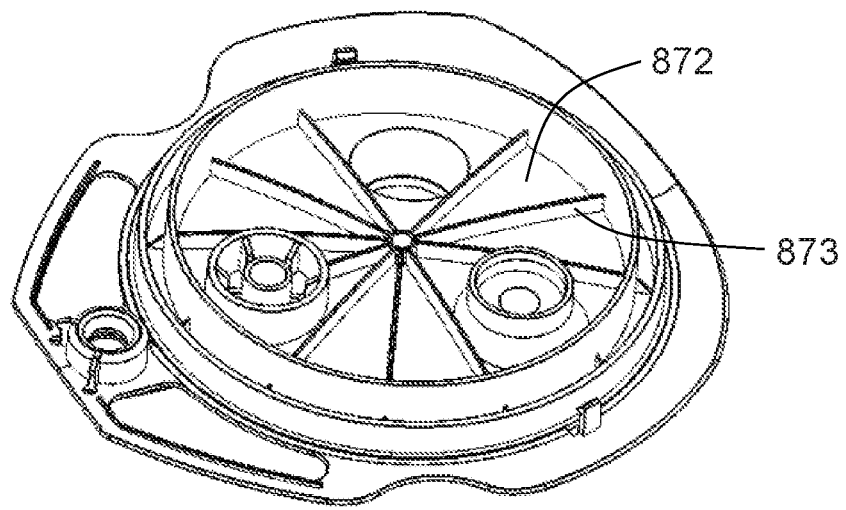
FIG. 29 is a bottom perspective view of a lid in accordance with aspects of the present disclosure.
Figure 30:
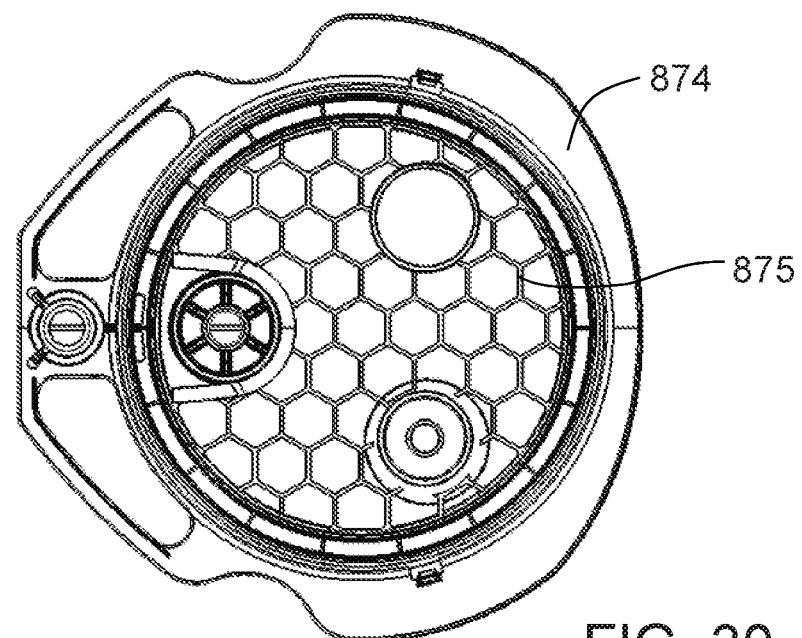
FIG. 30 is a bottom view of a lid in accordance with aspects of the present disclosure.
Figure 31:
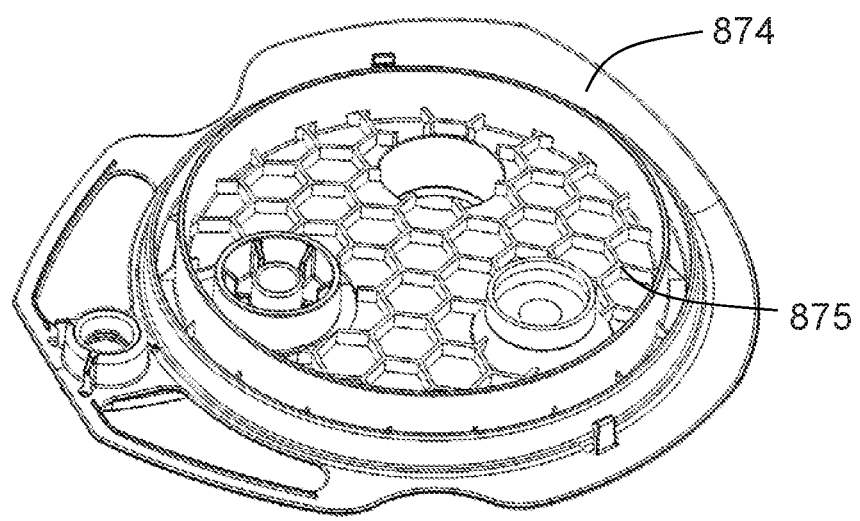
Figure 32:
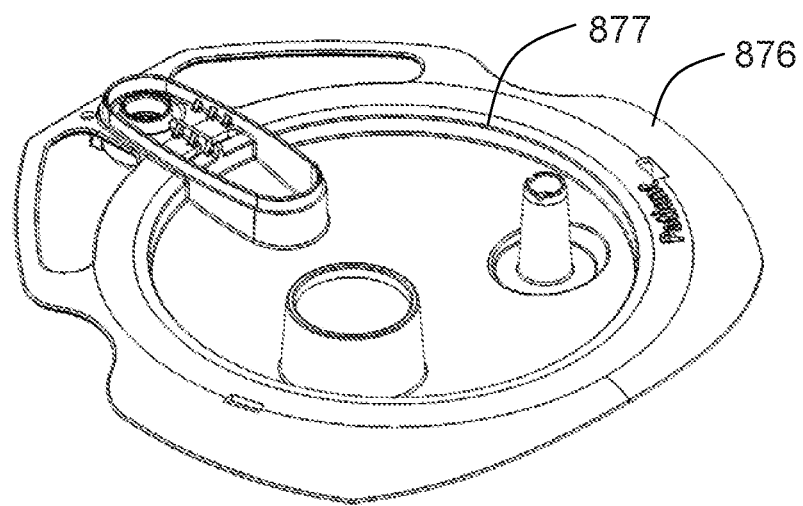
FIG. 32 is a perspective view of a lid in accordance with aspects of the present disclosure.
Figure 33:
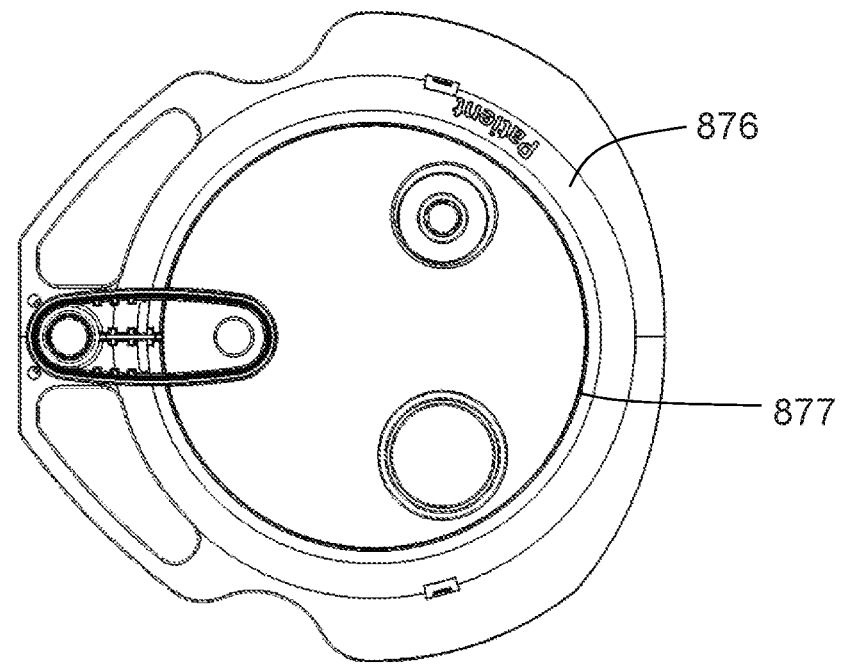
FIG. 33 is a top view of a lid in accordance with aspects of the present disclosure.

Although the lid 811 is illustrated as having a central portion with a generally convex-shaped upper surface, in various alternative embodiments, the lid may include features designed to increase strength, to reduce flexure or deflection of the lid as a result of the pressure differential across the lid during use, and/or to enhance the seal between the lid and the canister and/or between the lid and the auxiliary vacuum source connector during use. For example, in the embodiment illustrated in FIGS. 23-27, the lid 870 includes a concave-shaped center portion 871 that facilitates distribution of tensile stresses in the lid 870 during use. As illustrated in FIG. 27, the lid 870 may include tethered caps 882 attached to the lid via lid vacuum passageway cap 883. In the embodiment illustrated in FIGS. 28-29, the lid 872 includes one or more radial ribs 873 at the underside of the lid 872. In another example embodiment illustrated in FIGS. 30-31, the lid 874 includes a honeycomb pattern of ribs 875 at the underside of the lid 874. In the embodiment of FIGS.

Figure 36:
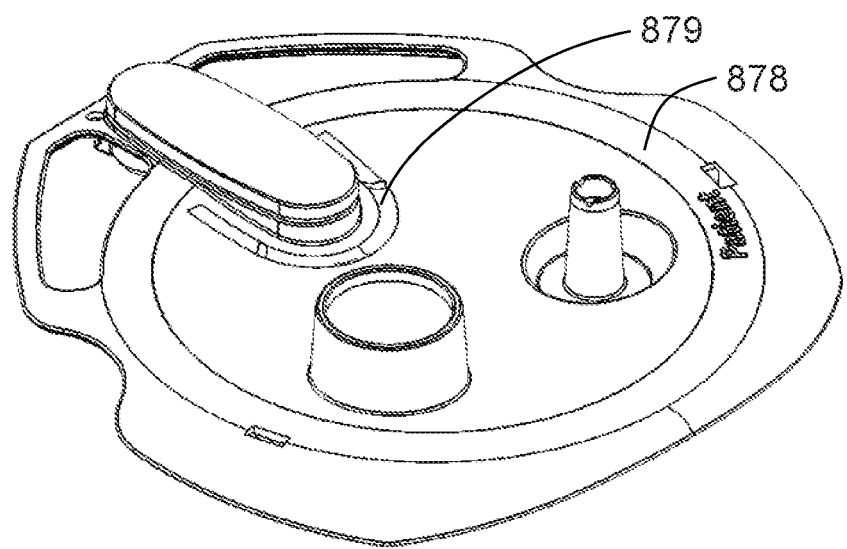
FIG. 36 is a perspective view of a lid in accordance with aspects of the present disclosure.
Figure 37:
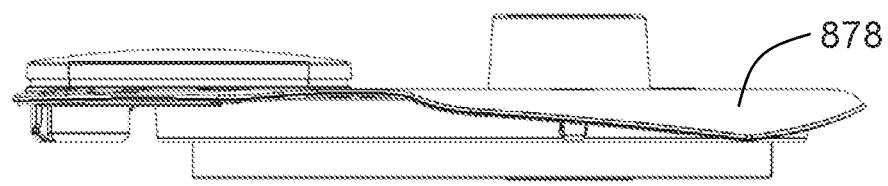
FIG. 37 is a side view of a lid in accordance with aspects of the present disclosure.
Figure 38:
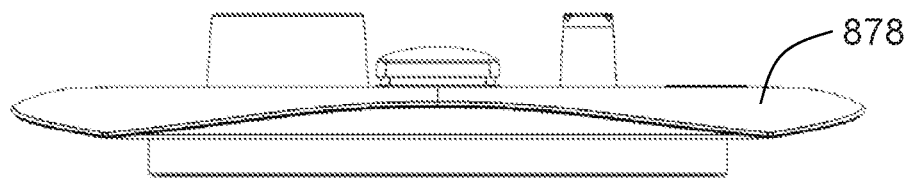
FIG. 38 is a front view of a lid in accordance with aspects of the present disclosure.

32-35, the lid 876 includes an annular step 877. In the embodiment of FIGS. 36-38, the lid 878 includes a relief recess 879 configured to reduce stresses acting on the lid vacuum passageway wall portions 881 as a result of downward deflection of the central portions of the lid 878 during use. The ordinarily skilled artisan will appreciate that a variety of features and methods may be utilized to enhance the strength, rigidity, sealing capabilities, and other performance characteristics of the lid.

Figure 39:
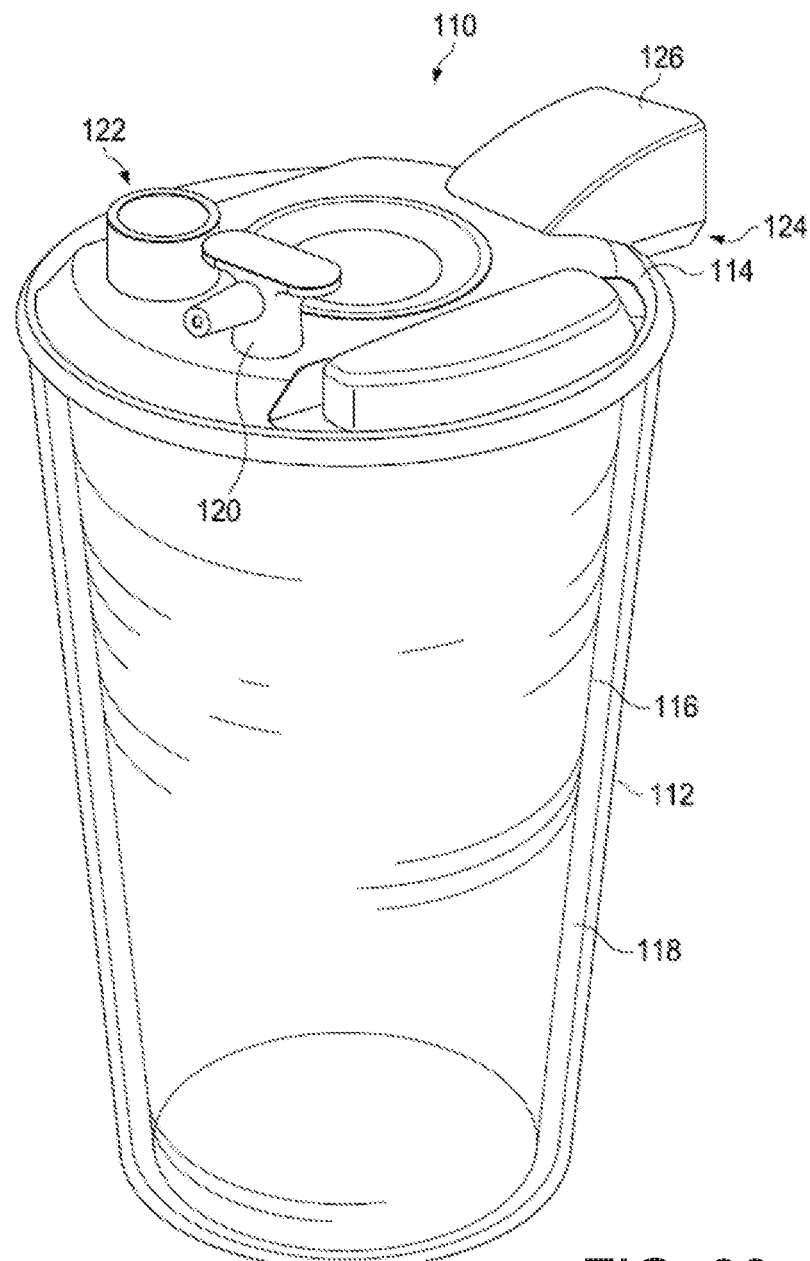
FIG. 39 is a perspective view of a canister assembly in accordance with aspects of the present disclosure.

Another embodiment of a fluid collection system in accordance with the present disclosure is illustrated in FIGS. 39-46. In this embodiment, the fluid collection system 900 includes a fluid collection canister assembly 910 as illustrated in FIG. 39. The canister assembly 910 includes a substantially rigid canister 912, a substantially rigid lid 914, and a flexible liner 916. The canister 912 forms a receptacle having an opening at an upper end. When coupled together as illustrated, the lid 914 and the canister 912 define a substantially sealed interior space hereinafter referred to as the interior of the canister. The flexible liner 916 is secured to the underside of the lid 914 and together the liner 916 and the lid 914 define a substantially sealed interior space hereinafter referred to as the interior of the liner. When the lid 914 is coupled to the canister 912 as illustrated, the liner 916 is disposed within the interior of the canister 912 such that the interior of the liner is also disposed within the interior of the canister. A space remaining between the interior surface of the canister 912 and the exterior surface of the liner 914 may be referred to herein as the interstitial space 918. The lid 914 includes a patient port 920, a tandem port 922 (not directly visible), and a lid vacuum port 924 (not directly visible) at the underside of the projection member 926.

Figure 40:
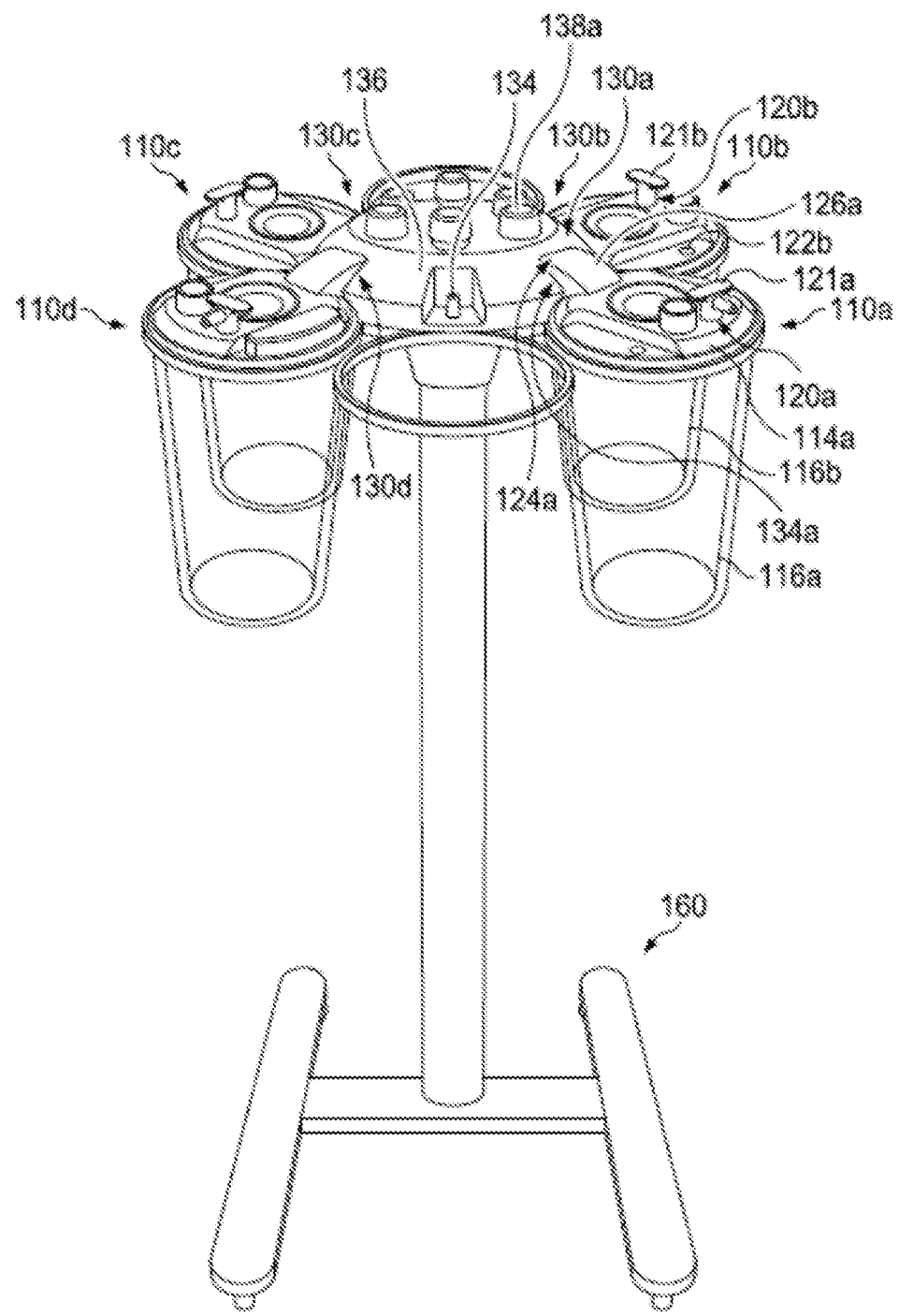
FIG. 40 is a perspective view of a fluid collection system in accordance with aspects of the present disclosure.
Figure 41:
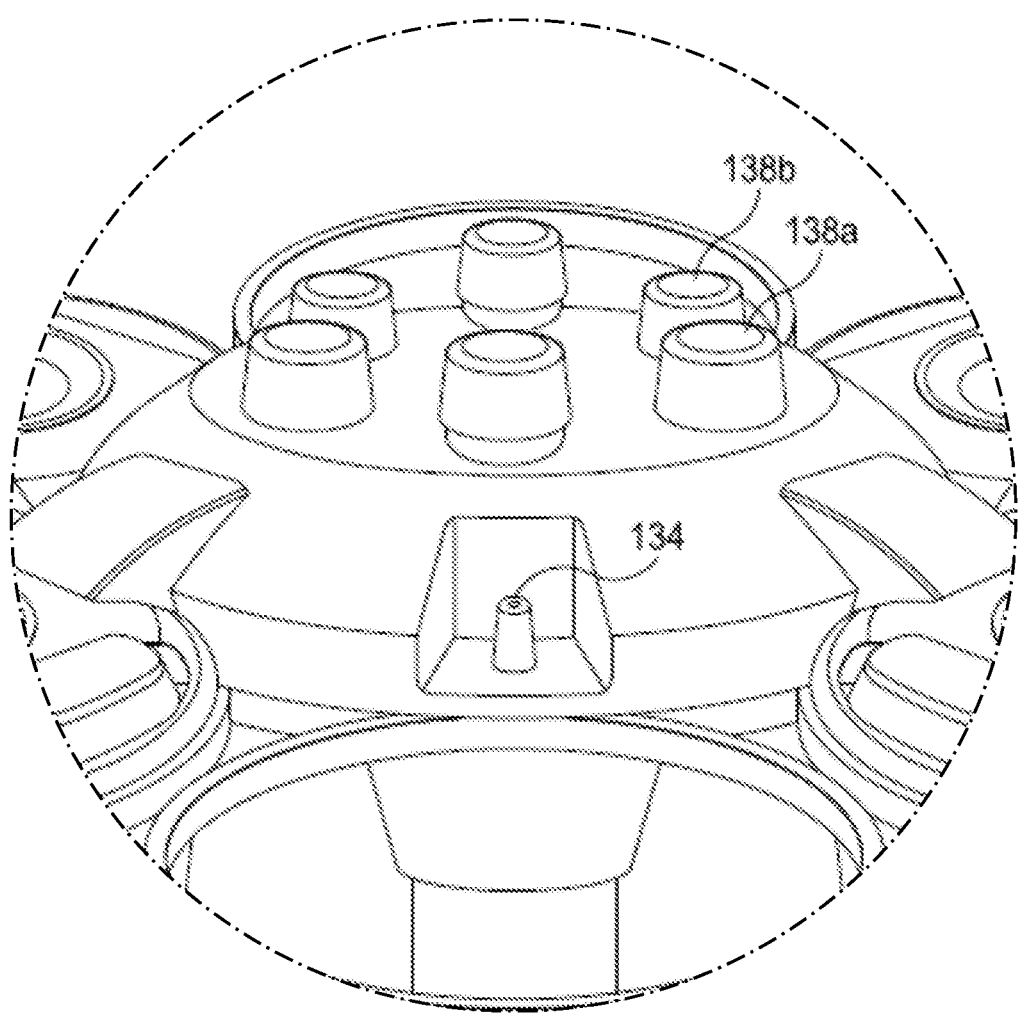
FIG. 41 is a detail perspective view of a fluid collection system in accordance with aspects of the present disclosure.

Referring to FIGS. 40-41, four canister assemblies 910a-910d are illustrated mounted on a rolling support stand 960. Vacuum port 924a cooperates with mateable vacuum port 934a provided at the mounting interface 930a of vacuum manifold 936. Vacuum ports such as vacuum port 934 provided at each mounting interface 930a-930d, are selectively in fluid communication with a suction source (not shown) such as a medical facility's central vacuum line via vacuum manifold 936. Negative pressure provided at the suction source is communicated via vacuum manifold 936 through vacuum ports 934a and 924a through a channel or passage (not shown) in the lid 914a, similar to the lid vacuum passageways 107, 607, and 807 of the foregoing embodiments, to the interior of the liner 916a, and from the interior of the liner 916a through patient port 920a to the patient or suction instrument via suction tubing (not shown). Suction at the open end of the suction tubing draws liquids, gasses, vapors, solids, and particulates through the suction tubing and into the interior of the liner. In general, liquids and solids are collected in the liner, while gasses pass through a filter at the vacuum port (not shown) of the lid 914a, out of the canister assembly 910a, and toward the suction source.

Figure 42:
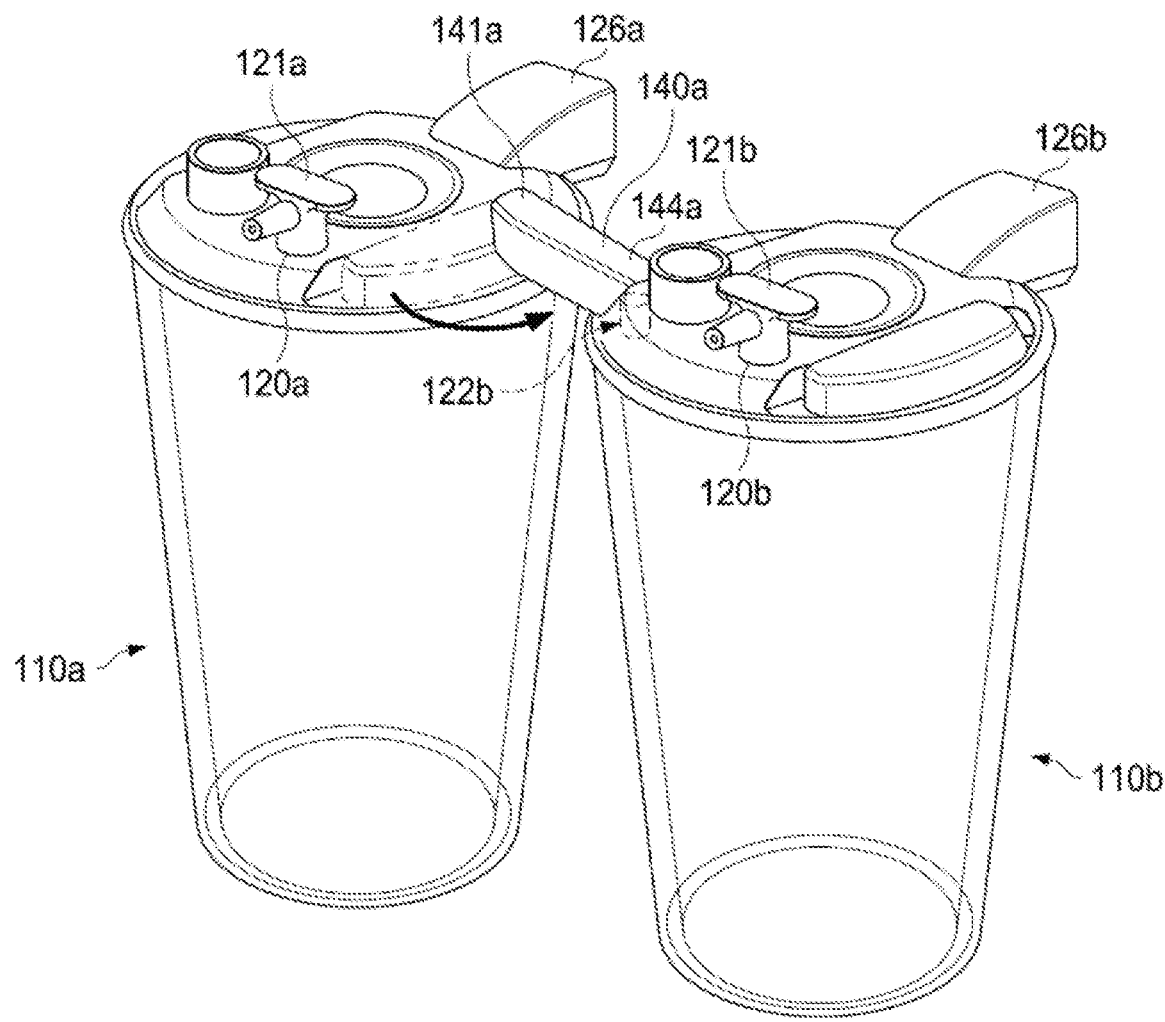
FIG. 42 is a perspective view of canister assemblies in accordance with aspects of the present disclosure.
Figure 43:
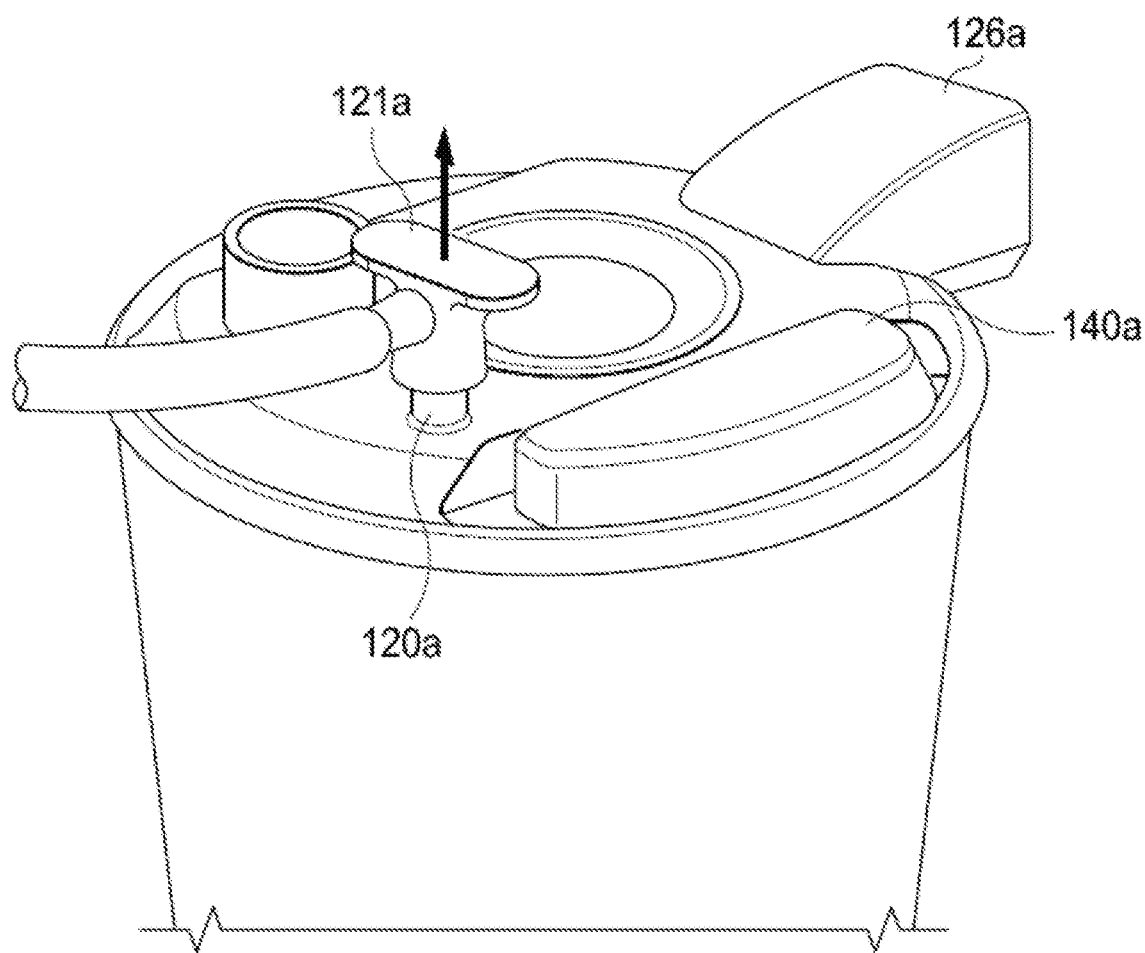
FIG. 43 is a detail perspective view of a canister assembly in accordance with aspects of the present disclosure.

When coupled in series, valved port connector 921a may be pulled up to close the port, as illustrated in FIG. 43. Alternatively, vacuum valve and indicator 938a may be closed to prevent suction from being supplied to the interior of the liner 916b via the vacuum channel of projection member 926a. As best seen in FIG. 42, tandem connector arm 940a may be rotated about proximal end 941a such that a distal port provided at a distal end 944a of the arm 940a couples with a tandem port 922b of a second canister assembly 910b. Thus, vacuum present at the interior of the liner 916a is communicated to the interior of the second liner 916b and to the patient or suction instrument via patient port 920b of the second canister assembly 910b. Collected fluid enters the interior of the second liner 916b via patient port 920b. When the fluid rises to the level of the filter in the second canister, the filter swells and seals off vacuum port 924b to prevent fluid from entering the vacuum manifold. Vacuum applied via tandem connector arm 940a is present at tandem connector 922b and thus draws fluid into the interior of flexible liner 916a of the first canister assembly 910a. A similar configuration may be repeated to connect additional canister assemblies in series to provide for additional fluid collection volume capacity. Tandem connector arm 940a includes a shutoff valve (not shown) that is closed to prevent fluid or vacuum from passing through the arm when the arm is rotated toward the center of the lid to a closed position, and is opened to permit fluid and vacuum communication through the arm when the arm is rotated away from the lid (i.e., when the arm is extended) to an open state. Accordingly, lids such as lid 914a may be used as a standalone canister or may be employed in a serial configuration with reduced risk of spills and leakages.

Figure 44:
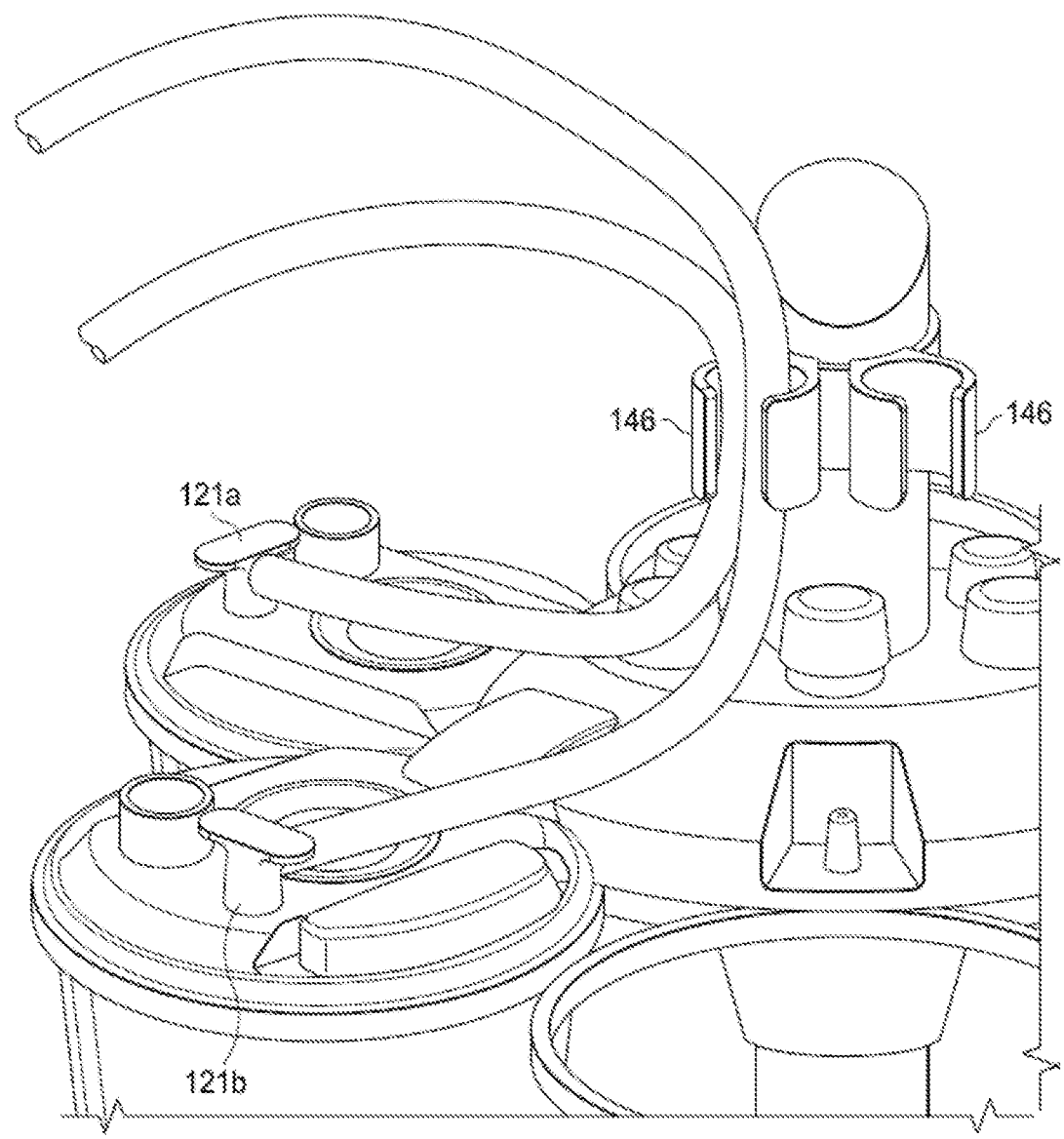
FIG. 44 is a detail perspective view of a fluid collection system in accordance with aspects of the present disclosure.

Referring to FIG. 44, valved port connector 921a is rotatable about its vertical axis to better accommodate various tubing positions, and tubing management guides 946 can be used to restrain and route tubing in various configurations.

Figure 45:
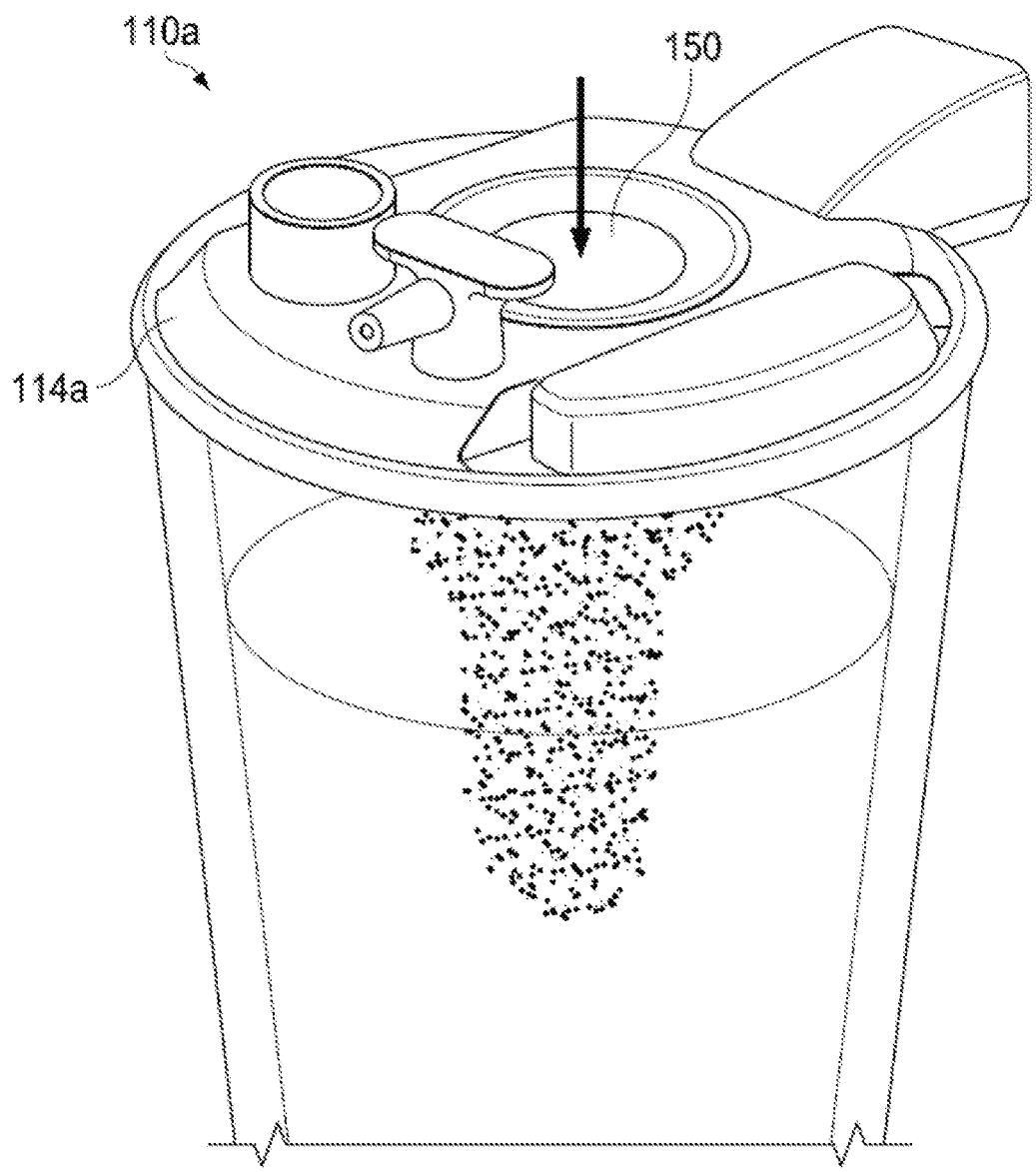
FIG. 45 is a detail perspective view of a canister assembly in accordance with aspects of the present disclosure.
Figure 46A:
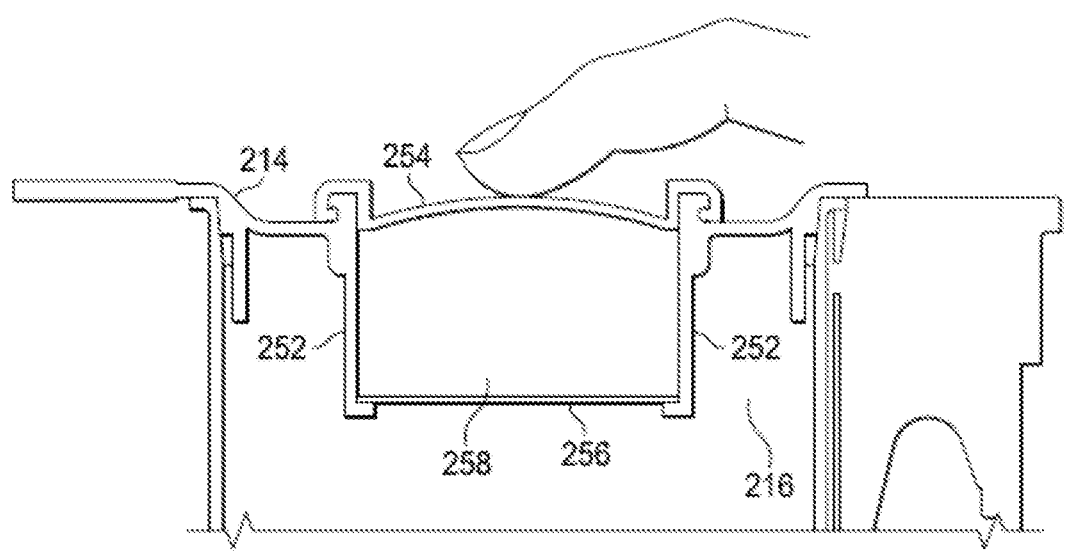
FIGS. 46A-46C are views of a chemical agent release mechanism in accordance with aspects of the present disclosure.
Figure 46B:
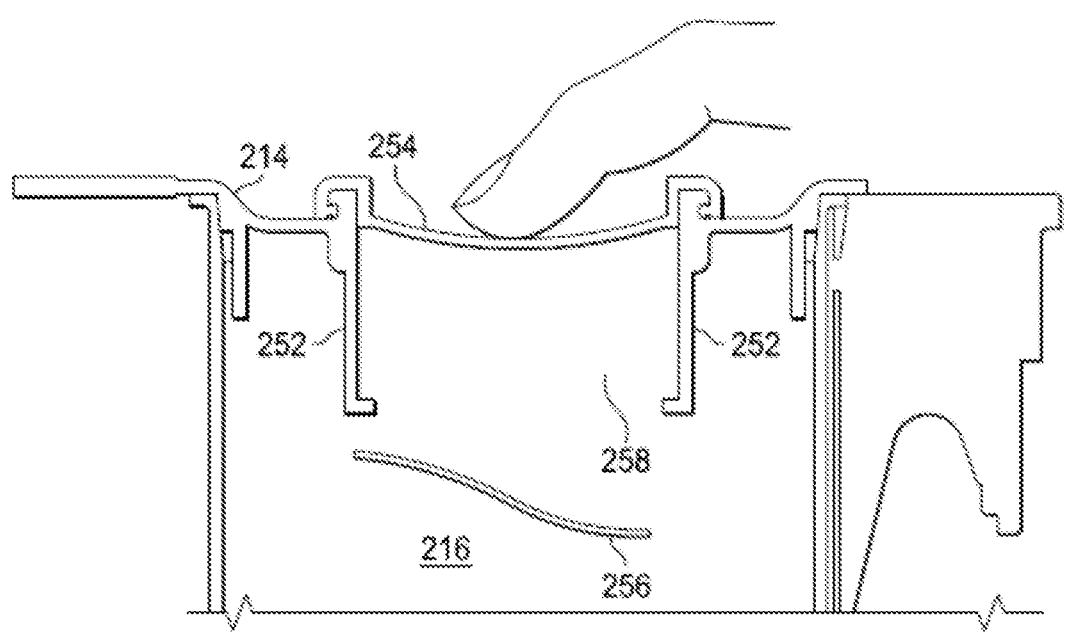
Figure 46C:
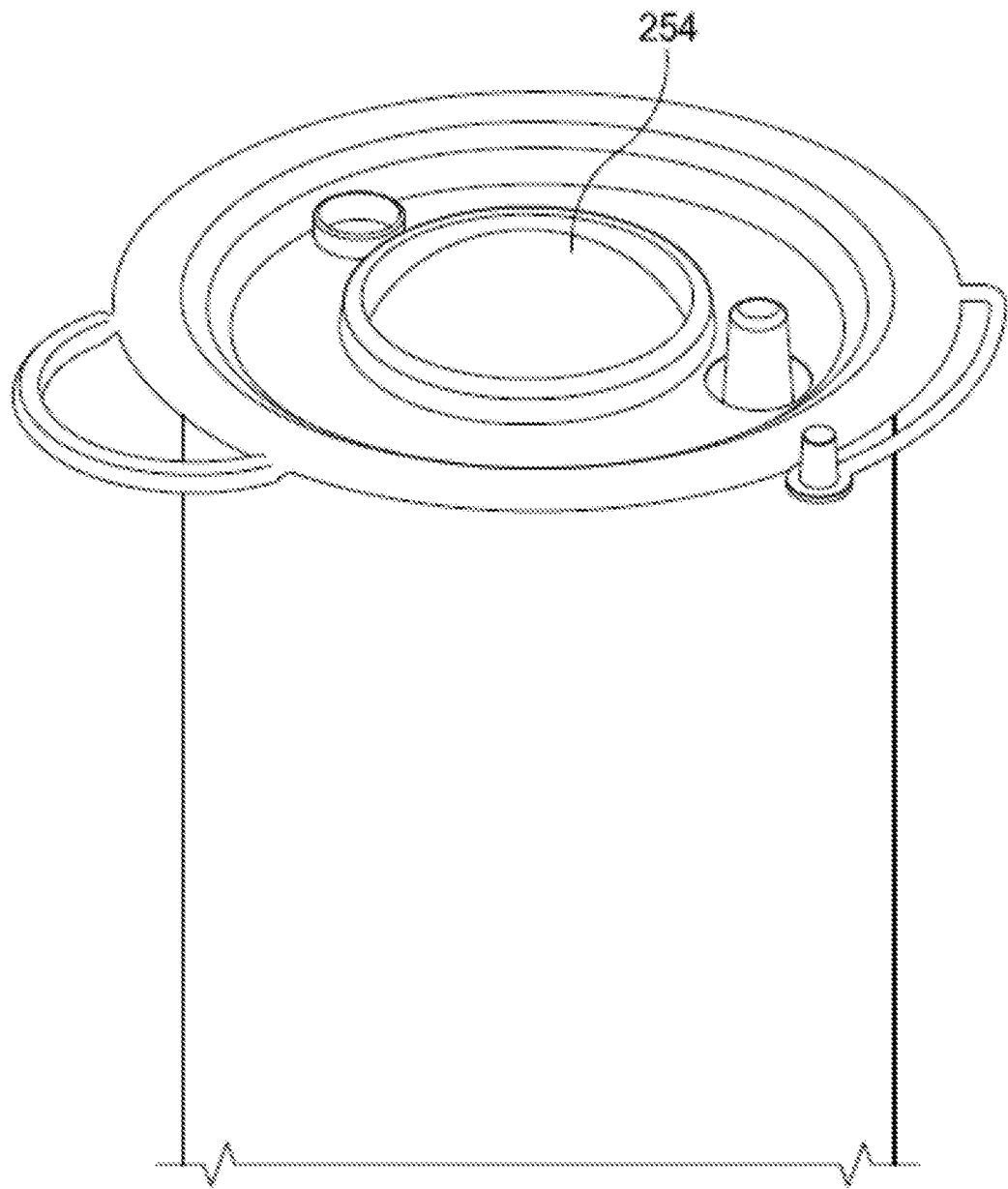

As illustrated in FIG. 45, chemical agent delivery mechanism 950 may be actuated to dispense a chemical agent into the interior of the liner 916a to treat fluids collected therein. In another embodiment, the lid 980 includes a generally cylindrical wall 984 defining an aperture in lid 980, as illustrated in FIGS. 46A-46C. A flexible domed cap 986 seals the top opening of the aperture, and a micro laser-perforated film seal 988 covers the bottom of the aperture, thereby restraining the chemical agent in a reservoir 990. Upon depression of the domed cap 986, the perforated film seal 988 is ruptured, and the chemical agents contained in the reservoir 990 are released into the interior of the liner 982.

While aspects of the present invention have been described and illustrated with reference to one or more variations thereof, it is not the intention of the applicant that these aspects be restricted to such detail. Rather, it is the intention of the applicant that aspects of the present invention be defined by all equivalents, both suggested hereby and known to those of ordinary skill in the art, of the variations falling within the scope thereof. Further the features of the aspects above may be combined or substituted to create an aspect of the disclosure having any combination of features discussed above.

| Key for Reference Characters | |
|---|---|
| Number | Part Name |
| 100 | fluid collection system |
| 101 | canister assembly |
| 102 | holder |
| 104 | accessory opening |
| 106 | tandem port |
| 107 | lid vacuum passageway |
| 108 | lid vacuum passageway cap |
| 109 | mounting portion |
| 109a | vacuum opening |
| 110 | patient port |
| 111 | lid |
| 112 | canister |
| 112a | canister wall |

-continued

| Key for Reference Characters | |
|---|---|
| Number | Part Name |
| 113 | liner, semi-flexible liner |
| 114 | manifold base |
| 115 | auxiliary vacuum source connector |
| 116 | manifold body |
| 117 | canister receiving portion |
| 118 | vacuum source lid |
| 119 | manifold |
| 120 | vacuum source connector |
| 121 | port cap |
| 122 | control valve |
| 123 | common vacuum chamber |
| 124 | control valve receiving portion |
| 125 | canister opening |
| 128 | guide slot |
| 130 | base |
| 131 | guide flange |
| 133 | stop |
| 134 | connector receiving portion |
| 135 | connector portion |
| 136 | mounting base portion |
| 138 | filter/valve |
| 140 | lever portion |
| 141 | O-ring |
| 142 | snap-fit portion |
| 143 | snap-fit receiving portion |
| 144 | stop |
| 145 | valve passageway |
| 146 | valve opening |
| 150 | valve |
| 152 | flexible material |
| 154 | valve opening |
| 200 | interstitial space |
| 202 | interstitial vacuum passageway |
| 204 | primary vacuum passageway |
| 206 | junction |
| 208 | auxiliary vacuum source passageway |
| 600 | fluid collection system |
| 601 | canister assembly |
| 602 | handle |
| 606 | tandem port |
| 607 | lid vacuum passageway |
| 608 | lid vacuum passageway cap |
| 609 | mounting portion |
| 610 | patient port |
| 611 | lid |
| 612 | canister |
| 613 | liner, semi-flexible liner |
| 614 | manifold base |
| 615 | auxiliary vacuum source connector |
| 616 | manifold body |
| 617 | ring holder receiving portion |
| 619 | manifold |
| 620 | vacuum source connector |
| 621 | shoulder |
| 622 | control valve |
| 623 | common vacuum source passageway |
| 624 | control valve receiving portion |
| 625 | canister wall |
| 628 | guide slot |
| 630 | rolling stand |
| 631 | guide member |
| 634 | connector receiving portion |
| 635 | connector portion |
| 636 | seal |
| 637 | auxiliary vacuum source connector opening |
| 638 | filter/valve |
| 639 | filter/valve housing |
| 640 | knob portion |
| 642 | markings |
| 644 | writeable portion |
| 670 | ring holder |
| 671 | nozzle seal |
| 672 | nozzle |
| 675 | vacuum bulb |
| 677 | opening |

-continued

| Key for Reference Characters | |
|---|---|
| Number | Part Name |
| 678 | lid vacuum chamber |
| 680 | interstitial space |
| 682 | interstitial vacuum passageway |
| 684 | liner vacuum passageway |
| 688 | auxiliary vacuum source passageway |
| 690 | port caps |
| 691 | anchor |
| 695 | dome portion |
| 696 | seal |
| 698 | plug |
| 800 | fluid collection system |
| 801 | canister assembly |
| 802 | handle |
| 806 | tandem/accessory port |
| 807 | lid vacuum passageway |
| 808 | lid vacuum passageway cap |
| 809 | mounting portion |
| 810 | patient port |
| 811 | lid |
| 812 | canister |
| 813 | liner |
| 814 | manifold base |
| 815 | auxiliary vacuum source connector |
| 816 | manifold body |
| 817 | canister receiving portion |
| 818 | canister opening |
| 819 | manifold |
| 820 | main vacuum source connector |
| 822 | valve |
| 823 | common vacuum source passageway |
| 826 | valve body |
| 828 | relief vent |
| 830 | rolling stand |
| 838 | filter/valve |
| 840 | knob |
| 842 | interstitial vacuum passageway |
| 844 | valve passageway |
| 845 | upstream opening |
| 846 | downstream opening |
| 847 | seal pad |
| 848 | venting seal pad |
| 850 | lid vacuum port |
| 851 | lid protrusion |
| 852 | annular wall |
| 853 | guide member |
| 854 | canister lip |
| 855 | canister rim |
| 856 | lid tab |
| 857 | ramped protrusion |
| 858 | lid flanges |
| 859 | recess |
| 862 | mounting rails |
| 864 | mounting slots |
| 866 | Retention tabs |
| 868 | canister flanges |
| 869 | canister rib |
| 870 | lid |
| 871 | center portion |
| 872 | lid |
| 873 | rib |
| 874 | lid |
| 875 | ribs |
| 876 | lid |
| 877 | step |
| 878 | lid |
| 879 | recess |
| 880 | interstitial space |
| 881 | lid vacuum passageway wall portion |
| 882 | central manifold piece |
| 888 | auxiliary vacuum source passageway |
| 889 | downstream portion |
| 900 | fluid collection system |
| 910 | canister assembly |
| 912 | canister |
| 914 | lid |

-continued

| Key for Reference Characters | |
|---|---|
| Number | Part Name |
| 916 | liner |
| 918 | interstitial space |
| 920 | patient port |
| 921 | port connector |
| 922 | tandem port |
| 924 | lid vacuum port |
| 926 | projection member |
| 930 | mounting interface |
| 934 | vacuum port |
| 936 | manifold |
| 938 | vacuum valve/indicator |
| 940 | tandem connector arm |
| 941 | tandem connector arm proximal end |
| 944 | tandem connector arm distal end |
| 946 | tubing management guide |
| 950 | delivery mechanism |
| 960 | support stand |
| 980 | lid |
| 982 | liner |
| 984 | lid wall |
| 986 | domed cap |
| 988 | film seal |
| 990 | reservoir |

The invention claimed is:

1. A fluid collection system, comprising:
an outer container, which is a canister body having a protruding mounting portion;
a removable lid coupled to the outer container and having an attached liner, the lid and the outer container encompassing the liner, wherein an interstitial space is defined between an outer surface of the liner and an inner surface of the outer container;
a vacuum passage located within the outer container comprising:
a first passage portion in communication with a vacuum source,
a liner vacuum passage in communication with the first passage portion and the interior of the liner, and
an interstitial vacuum passage in communication with the first passage portion and the interstitial space,
wherein the first passage portion is included internally in the protruding mounting portion,
wherein the liner vacuum passage is located in the lid and communicates directly with the first passage portion included internally in the protruding mounting portion, and
wherein the interstitial vacuum passage branches off the first passage portion at a junction provided in the mounting portion of the canister body.

2. The fluid collection system of claim 1, where the interstitial vacuum passage is located in the outer container.

3. The fluid collection system of claim 1, wherein the first passage portion is located within the outer container.

4. The fluid collection system of claim 3, wherein the liner vacuum passage is also located in the outer container.

5. The fluid collection system of claim 4, wherein the interstitial vacuum passage is located within the outer container.

6. The fluid collection system of claim 4, wherein the interstitial vacuum passage is located in the lid and the outer container.

7. The fluid collection system of claim 1, wherein at least a portion of the first passage portion is located in the lid.

8. The fluid collection system of claim 7, wherein the interstitial vacuum passage is located within the lid.

9. The fluid collection system of claim 1, wherein a cap seals at least a portion of the liner vacuum passage at a side of the lid facing away from the liner.

10. The fluid collection system of claim 1, further comprising:
a filter located in communication with the liner vacuum passage.

11. The fluid collection system of claim 10, wherein the filter is attached to the lid.

12. The fluid collection system of claim 10, wherein the filter is located within the liner vacuum passage.

13. The fluid collection system of claim 10, wherein the lid includes a housing portion opening, wherein the filter is housed within the housing portion opening, and wherein the housing portion opening is sealed with a cap.

14. The fluid collection system of claim 1, wherein the lid includes a chemical agent housing portion.

15. The fluid collection system of claim 14, wherein the chemical agent housing portion includes a seal located at a side of the lid facing the liner.

16. The fluid collection system of claim 15, wherein the chemical agent housing portion includes a flexible wall located at a side of the lid facing away from the liner.

* * * * *